(12) United States Patent
Chandler et al.

(10) Patent No.: US 10,525,240 B1
(45) Date of Patent: Jan. 7, 2020

(54) SINO-NASAL RINSE DELIVERY DEVICE WITH AGITATION, FLOW-CONTROL AND INTEGRATED MEDICATION MANAGEMENT SYSTEM

(71) Applicant: Sandler Scientific, LLC, Montgomery, AL (US)

(72) Inventors: Stephen W. Chandler, Montgomery, AL (US); David W. Sanso, Morrison, CO (US)

(73) Assignee: Sandler Scientific LLC, Montgomery, AL (US)

( * ) Notice: Subject to any disclaimer, the term of this patent is extended or adjusted under 35 U.S.C. 154(b) by 0 days.

(21) Appl. No.: 16/451,123

(22) Filed: Jun. 25, 2019

Related U.S. Application Data

(60) Provisional application No. 62/691,010, filed on Jun. 28, 2018, provisional application No. 62/782,889, (Continued)

(51) Int. Cl.
*A61M 31/00* (2006.01)

(52) U.S. Cl.
CPC ....... *A61M 31/00* (2013.01); *A61M 2202/064* (2013.01); *A61M 2202/066* (2013.01); (Continued)

(58) Field of Classification Search
CPC ............ A61M 31/00; A61M 2202/064; A61M 2202/066; A61M 2205/076; (Continued)

(56) References Cited

U.S. PATENT DOCUMENTS 2,434,875 A 1/1948 Turnbull et al.
2,493,326 A 1/1950 Trinder
(Continued)

FOREIGN PATENT DOCUMENTS

CA 2266958 A1 10/1999
EP 2522386 A2 11/2012
(Continued)

OTHER PUBLICATIONS

Agro, et al., "Lightwand intubation using the Trachlight(TM): a brief review of current knowledge," Canadian Journal of Anesthesia, (2000), pp. 592-599.
(Continued)

*Primary Examiner* — Shefali D Patel
(74) *Attorney, Agent, or Firm* — Atlanta Technology Law; Luke Anderson

(57) ABSTRACT

A device, a system and a method are provided to accurately apply a medically beneficial substance directly to a laterally or superiorly located paranasal sinus cavity. When the device is assembled with a solution in a reservoir, and inverted such that the reservoir is above an input apparatus and a housing, weight of the solution pushes down on a diaphragm creating a negative pressure on the diaphragm, which prevents air from entering the reservoir and prevents a liquid from flowing out of the reservoir. Applying a positive pressure to a bottom of the diaphragm causes the diaphragm to open and allows air to flow into the reservoir. When a user creates the positive pressure by exhaling air into the device the act of exhaling causes the user's choana to close. Thereby any solution introduced into the user's sino-nasal cavity will remain contained within the user's sino-nasal cavity increasing effectiveness of treatment and decreasing user discomfort including gagging, choking, and inner ear disturbance. When the positive pressure on the bottom of the diaphragm is removed, the flow of the liquid from the reservoir stops.

18 Claims, 14 Drawing Sheets

Related U.S. Application Data filed on Dec. 20, 2018, provisional application No. 62/782,898, filed on Dec. 20, 2018.

(52) U.S. Cl.
CPC ... *A61M 2205/076* (2013.01); *A61M 2205/75* (2013.01); *A61M 2210/0618* (2013.01); *A61M 2210/0681* (2013.01)

(58) Field of Classification Search
CPC ...... A61M 2205/75; A61M 2205/7545; A61M 2210/0618; A61M 2210/0681; A61H 35/04; A61H 2205/023; A61J 3/02
See application file for complete search history.

(56) References Cited

U.S. PATENT DOCUMENTS

| | | |
|---|---|---|
| 2,847,997 A | 8/1958 | Tibone |
| 2,936,760 A | 5/1960 | Gants |
| 3,049,125 A | 8/1962 | Kriwkowitsch |
| 3,664,330 A | 5/1972 | Deutsch |
| 3,747,595 A | 7/1973 | Grossan |
| 3,766,924 A | 10/1973 | Pidgeon |
| 3,800,788 A | 4/1974 | White |
| 3,850,176 A | 11/1974 | Gottschalk |
| 3,903,893 A | 9/1975 | Scheer |
| 4,592,357 A | 6/1986 | Ersek |
| 4,606,346 A | 8/1986 | Berg et al. |
| 4,819,619 A | 4/1989 | Augustine et al. |
| 4,883,465 A | 11/1989 | Brennan |
| 4,886,493 A | 12/1989 | Yee |
| 4,887,593 A | 12/1989 | Wiley et al. |
| 5,024,658 A | 6/1991 | Kozlov et al. |
| 5,116,311 A | 5/1992 | Lofstedt |
| 5,189,727 A | 2/1993 | Guerreri |
| 5,193,525 A | 3/1993 | Silverstein et al. |
| 5,213,115 A | 5/1993 | Zytkovicz et al. |
| 5,215,536 A | 6/1993 | Lampropoulos et al. |
| 5,242,400 A | 9/1993 | Blake et al. |
| 5,370,640 A | 12/1994 | Kolff |
| 5,446,070 A | 8/1995 | Mantelle |
| 5,462,553 A | 10/1995 | Dolgin |
| 5,483,951 A | 1/1996 | Frassica et al. |
| 5,514,128 A | 5/1996 | Hillsman et al. |
| 5,531,676 A | 7/1996 | Edwards et al. |
| 5,534,242 A | 7/1996 | Henry |
| 5,546,964 A | 8/1996 | Stangerup |
| 5,599,304 A | 2/1997 | Shaari |
| 5,626,553 A | 5/1997 | Frassica et al. |
| 5,647,847 A | 7/1997 | Lafontaine et al. |
| 5,667,476 A | 9/1997 | Frassica et al. |
| 5,676,635 A | 10/1997 | Levin |
| 5,685,822 A | 11/1997 | Harhen |
| 5,718,666 A | 2/1998 | Alarcon |
| 5,735,817 A | 4/1998 | Shantha |
| 5,752,971 A | 5/1998 | Rosenbluth et al. |
| 5,792,100 A | 8/1998 | Shantha |
| 5,819,727 A | 10/1998 | Linder |
| 5,827,177 A | 10/1998 | Oneda et al. |
| 5,827,224 A | 10/1998 | Shippert |
| 5,858,331 A | 1/1999 | Henry |
| 5,876,329 A | 3/1999 | Harhen |
| 6,027,478 A | 2/2000 | Katz |
| 6,106,496 A | 8/2000 | Arnissolle |
| 6,174,280 B1 | 1/2001 | Oneda et al. |
| 6,190,330 B1 | 2/2001 | Harhen |
| 6,258,101 B1 | 7/2001 | Blake et al. |
| 6,322,542 B1 | 11/2001 | Nilson et al. |
| 6,350,231 B1 | 2/2002 | Ailinger et al. |
| 6,350,465 B1 | 2/2002 | Jonnalagadda et al. |
| 6,394,093 B1 | 5/2002 | Lethi |
| 6,413,499 B1 | 7/2002 | Clay |
| 6,432,986 B2 | 8/2002 | Levin |
| 6,461,294 B1 | 10/2002 | Oneda et al. |
| 6,491,940 B1 | 12/2002 | Levin |
| 6,529,756 B1 | 3/2003 | Phan et al. |
| 6,530,881 B1 | 3/2003 | Ailinger et al. |
| 6,579,582 B1 | 6/2003 | Harhen et al. |
| D478,987 S | 8/2003 | Groenke et al. |
| 6,607,546 B1 | 8/2003 | Murken |
| 6,669,711 B1 | 12/2003 | Noda |
| 6,677,321 B1 | 1/2004 | Levin |
| 6,693,670 B1 | 2/2004 | Stark |
| 6,715,485 B1 * | 4/2004 | Djupesland ....... A61M 15/0028 128/203.15 |
| 6,733,440 B2 | 5/2004 | Ailinger et al. |
| 6,740,030 B2 | 5/2004 | Martone et al. |
| 6,758,840 B2 | 7/2004 | Knox |
| 6,770,080 B2 | 8/2004 | Kaplan et al. |
| 6,793,661 B2 | 9/2004 | Hamilton et al. |
| 6,822,213 B2 | 11/2004 | Stark |
| 6,853,858 B2 | 2/2005 | Shalev |
| 6,902,535 B2 | 6/2005 | Eberhart et al. |
| 7,025,923 B2 | 4/2006 | Harhen et al. |
| 7,056,284 B2 | 6/2006 | Martone et al. |
| 7,056,287 B2 | 6/2006 | Taylor et al. |
| 7,081,097 B2 | 7/2006 | Martone et al. |
| 7,112,578 B2 | 9/2006 | Levin |
| D530,815 S | 10/2006 | Murphy et al. |
| 7,117,033 B2 | 10/2006 | Shalev et al. |
| 7,120,489 B2 | 10/2006 | Shalev et al. |
| 7,131,969 B1 | 11/2006 | Hovda et al. |
| D534,216 S | 12/2006 | Makower et al. |
| 7,146,209 B2 | 12/2006 | Gross et al. |
| 7,169,161 B2 | 1/2007 | Bonnette et al. |
| 7,190,998 B2 | 3/2007 | Shalev et al. |
| D544,602 S | 6/2007 | Hughett et al. |
| 7,336,309 B2 | 2/2008 | Stark |
| 7,361,168 B2 | 4/2008 | Makower et al. |
| 7,377,901 B2 | 5/2008 | Djupesland et al. |
| 7,410,480 B2 | 8/2008 | Muni et al. |
| 7,419,497 B2 | 9/2008 | Muni et al. |
| 7,462,175 B2 | 12/2008 | Chang et al. |
| 7,500,971 B2 | 3/2009 | Chang et al. |
| 7,507,200 B2 | 3/2009 | Okada |
| 7,520,876 B2 | 4/2009 | Ressemann et al. |
| 7,559,925 B2 | 7/2009 | Goldfarb et al. |
| 7,561,919 B2 | 7/2009 | Shalev et al. |
| 7,636,597 B2 | 12/2009 | Gross et al. |
| 7,640,062 B2 | 12/2009 | Shalev |
| 7,641,644 B2 | 1/2010 | Chang et al. |
| 7,642,563 B2 | 1/2010 | Kang et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,678,099 B2 | 3/2010 | Ressemann et al. |
| 7,684,859 B2 | 3/2010 | Shalev et al. |
| 7,704,259 B2 | 4/2010 | Kaplan et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,729,759 B2 | 6/2010 | Shalev et al. |
| 7,740,642 B2 | 6/2010 | Becker |
| 7,749,515 B2 | 7/2010 | Blumenfeld |
| 7,753,929 B2 | 7/2010 | Becker |
| 7,753,930 B2 | 7/2010 | Becker |
| 7,771,409 B2 | 8/2010 | Chang et al. |
| 7,785,315 B1 | 8/2010 | Muni et al. |
| 7,799,337 B2 | 9/2010 | Levin |
| 7,803,150 B2 | 9/2010 | Chang et al. |
| 7,837,672 B2 | 11/2010 | Intoccia |
| 7,841,337 B2 * | 11/2010 | Djupesland ....... A61M 15/0091 128/200.23 |
| 7,842,062 B2 | 11/2010 | Keith et al. |
| 7,854,744 B2 | 12/2010 | Becker |
| 7,877,147 B2 | 1/2011 | Shalev et al. |
| 7,879,011 B2 | 2/2011 | Chang |
| 7,879,061 B2 | 2/2011 | Keith et al. |
| 7,908,000 B2 | 3/2011 | Shalev |
| 7,918,871 B2 | 4/2011 | Truitt et al. |
| D640,374 S | 6/2011 | Liu et al. |
| D643,115 S | 8/2011 | Gonzales et al. |

(56) References Cited

U.S. PATENT DOCUMENTS

| | | |
|---|---|---|
| 8,010,189 B2 | 8/2011 | Shalev |
| 8,012,084 B2 | 9/2011 | Machida |
| 8,025,635 B2 | 9/2011 | Eaton et al. |
| 8,052,693 B2 | 11/2011 | Shahoian |
| 8,080,000 B2 | 12/2011 | Makower et al. |
| 8,088,101 B2 | 1/2012 | Chang et al. |
| 8,090,433 B2 | 1/2012 | Makower et al. |
| 8,100,933 B2 | 1/2012 | Becker |
| 8,114,062 B2 | 2/2012 | Muni et al. |
| 8,114,113 B2 | 2/2012 | Becker |
| 8,118,757 B2 | 2/2012 | Morriss |
| 8,123,722 B2 | 2/2012 | Chang et al. |
| 8,142,422 B2 | 3/2012 | Makower et al. |
| D658,291 S | 4/2012 | Jenkins et al. |
| 8,146,400 B2 | 4/2012 | Goldfarb et al. |
| 8,172,828 B2 | 5/2012 | Chang et al. |
| 8,182,432 B2 | 5/2012 | Kim et al. |
| 8,190,389 B2 | 5/2012 | Kim et al. |
| 8,192,420 B2 | 6/2012 | Morriss et al. |
| 8,224,438 B2 | 7/2012 | Levin |
| 8,229,571 B2 | 7/2012 | Lorian et al. |
| 8,231,588 B2 | 7/2012 | Xia |
| 8,241,266 B2 | 8/2012 | Keith et al. |
| 8,241,641 B2 | 8/2012 | Blumenfeld |
| 8,249,700 B2 | 8/2012 | Clifford et al. |
| 8,277,478 B2 | 10/2012 | Drontle et al. |
| 8,282,667 B2 | 10/2012 | Drontle et al. |
| 8,308,709 B2 | 11/2012 | Chang |
| 8,313,520 B2 | 11/2012 | Barbut et al. |
| 8,317,816 B2 | 11/2012 | Becker |
| 8,337,454 B2 | 12/2012 | Eaton et al. |
| 8,348,969 B2 | 1/2013 | Keith et al. |
| 8,360,968 B2 | 1/2013 | Hadani |
| 8,388,600 B1 | 3/2013 | Eldredge |
| 8,388,642 B2 | 3/2013 | Muni et al. |
| 8,412,336 B2 | 4/2013 | Pless et al. |
| 8,414,473 B2 | 4/2013 | Jenkins et al. |
| 8,425,457 B2 | 4/2013 | John et al. |
| 8,425,488 B2 | 4/2013 | Clifford et al. |
| 8,435,290 B2 | 5/2013 | Clifford et al. |
| 8,439,687 B1 | 5/2013 | Morriss et al. |
| 8,452,392 B2 | 5/2013 | Morriss et al. |
| D683,852 S | 6/2013 | Gonzales et al. |
| 8,480,658 B1 | 7/2013 | Nakao |
| 8,485,199 B2 | 7/2013 | Morriss |
| 8,486,155 B2 | 7/2013 | McAlister et al. |
| 8,550,073 B2 | 10/2013 | Djupesland |
| 8,568,439 B2 | 10/2013 | Keith et al. |
| 8,585,728 B2 | 11/2013 | Keith et al. |
| 8,585,729 B2 | 11/2013 | Keith et al. |
| 8,623,043 B1 | 1/2014 | Keith et al. |
| 8,636,684 B2 | 1/2014 | Deem et al. |
| 8,657,846 B2 | 2/2014 | Keith et al. |
| 8,690,839 B2 | 4/2014 | Xia et al. |
| 8,702,626 B1 | 4/2014 | Kim et al. |
| 8,715,169 B2 | 5/2014 | Chang et al. |
| 8,721,591 B2 | 5/2014 | Chang et al. |
| 8,740,839 B2 | 6/2014 | Eaton et al. |
| 8,740,929 B2 | 6/2014 | Gopferich et al. |
| 8,747,389 B2 | 6/2014 | Goldfarb et al. |
| 8,764,709 B2 | 7/2014 | Chang et al. |
| 8,764,726 B2 | 7/2014 | Chang et al. |
| 8,764,729 B2 | 7/2014 | Muni et al. |
| 8,764,786 B2 | 7/2014 | Becker |
| 8,777,926 B2 | 7/2014 | Chang et al. |
| 8,801,670 B2 | 8/2014 | Drontle et al. |
| 8,828,041 B2 | 9/2014 | Chang et al. |
| 8,834,513 B2 | 9/2014 | Hanson et al. |
| 8,852,143 B2 | 10/2014 | Chang et al. |
| 8,858,551 B2 | 10/2014 | Naito |
| 8,858,586 B2 | 10/2014 | Chang et al. |
| 8,858,974 B2 | 10/2014 | Eaton et al. |
| 8,864,787 B2 | 10/2014 | Muni et al. |
| 8,876,794 B2 | 11/2014 | Xia |
| 8,882,795 B2 | 11/2014 | Drontle et al. |
| 8,888,686 B2 | 11/2014 | Drontle et al. |
| 8,894,614 B2 | 11/2014 | Muni et al. |
| 8,905,922 B2 | 12/2014 | Makower et al. |
| 8,905,980 B2 | 12/2014 | Xia |
| 8,910,629 B2 | 12/2014 | Djupesland et al. |
| 8,915,938 B2 | 12/2014 | Keith et al. |
| 8,932,276 B1 | 1/2015 | Morriss et al. |
| 8,954,149 B2 | 2/2015 | Shalev |
| 8,956,280 B2 | 2/2015 | Eversull et al. |
| 8,961,398 B2 | 2/2015 | Makower et al. |
| 8,978,647 B2 | 3/2015 | Djupesland et al. |
| 8,986,340 B2 | 3/2015 | Drontle et al. |
| 9,010,325 B2 | 4/2015 | Djupesland et al. |
| D730,515 S | 5/2015 | Shahidi Bonjar |
| 9,038,630 B2 | 5/2015 | Djupesland et al. |
| D735,848 S | 8/2015 | Dubuc et al. |
| D736,922 S | 8/2015 | Allen et al. |
| 9,248,266 B2 | 2/2016 | Chandler et al. |
| D772,406 S | 11/2016 | Sanso et al. |
| D773,644 S | 12/2016 | Djupesland |
| 9,510,743 B2 | 12/2016 | Chandler et al. |
| 9,516,995 B2 | 12/2016 | Chandler et al. |
| 9,649,456 B2 | 5/2017 | Djupesland et al. |
| 9,694,163 B2 | 7/2017 | Chandler et al. |
| 9,757,455 B2 | 9/2017 | Roberts et al. |
| 9,839,347 B2 | 12/2017 | Chandler et al. |
| 10,112,021 B2 | 10/2018 | Hafner |
| 2001/0002999 A1 | 6/2001 | Neuser et al. |
| 2001/0004644 A1 | 6/2001 | Levin |
| 2002/0010194 A1 | 1/2002 | Levin |
| 2002/0062119 A1 | 5/2002 | Zadno-Azizi |
| 2002/0161379 A1 | 10/2002 | Kaplan et al. |
| 2003/0120256 A1 | 6/2003 | Lary et al. |
| 2003/0133877 A1 | 7/2003 | Levin |
| 2003/0208249 A1 | 11/2003 | Chen |
| 2004/0064150 A1 | 4/2004 | Becker |
| 2004/0116958 A1 | 6/2004 | Gopferich et al. |
| 2004/0243172 A1 | 12/2004 | Hogle |
| 2005/0072430 A1 | 4/2005 | Djupesland |
| 2005/0080357 A1 | 4/2005 | Eberhart et al. |
| 2005/0113798 A1 | 5/2005 | Slater et al. |
| 2005/0124856 A1 | 6/2005 | Fujikura et al. |
| 2005/0228452 A1 | 10/2005 | Mourlas et al. |
| 2005/0240147 A1 | 10/2005 | Makower et al. |
| 2005/0245894 A1 | 11/2005 | Zadno-Azizi |
| 2005/0245906 A1 | 11/2005 | Makower et al. |
| 2005/0281751 A1 | 12/2005 | Levin |
| 2006/0004286 A1 | 1/2006 | Chang et al. |
| 2006/0004323 A1 | 1/2006 | Chang et al. |
| 2006/0063973 A1 | 3/2006 | Makower et al. |
| 2006/0095066 A1 | 5/2006 | Chang et al. |
| 2006/0106361 A1 | 5/2006 | Muni et al. |
| 2006/0155304 A1 | 7/2006 | Kaplan et al. |
| 2006/0161044 A1 | 7/2006 | Oneda et al. |
| 2006/0167439 A1 | 7/2006 | Kalser et al. |
| 2006/0189844 A1 | 8/2006 | Tien |
| 2006/0189847 A1 | 8/2006 | Yee et al. |
| 2006/0210605 A1 | 9/2006 | Chang et al. |
| 2007/0015964 A1 | 1/2007 | Eversull et al. |
| 2007/0020254 A1 | 1/2007 | Levin |
| 2007/0043327 A1 | 2/2007 | Knox |
| 2007/0073269 A1 | 3/2007 | Becker |
| 2007/0112257 A1 | 5/2007 | Hensler |
| 2007/0119451 A1 | 5/2007 | Wang et al. |
| 2007/0129705 A1 | 6/2007 | Trombley et al. |
| 2007/0129751 A1 | 6/2007 | Muni et al. |
| 2007/0135789 A1 | 6/2007 | Chang et al. |
| 2007/0142709 A1 | 6/2007 | Martone et al. |
| 2007/0167682 A1 | 7/2007 | Goldfarb et al. |
| 2007/0179518 A1 | 8/2007 | Becker |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0250105 A1 | 10/2007 | Ressemann et al. |
| 2007/0260264 A1 | 11/2007 | Nobis et al. |
| 2007/0265618 A1 | 11/2007 | Long |
| 2007/0267011 A1 | 11/2007 | Deem et al. |
| 2007/0282305 A1 | 12/2007 | Goldfarb et al. |
| 2007/0293726 A1 | 12/2007 | Goldfarb et al. |

(56) References Cited

U.S. PATENT DOCUMENTS

| | | |
|---|---|---|
| 2007/0293727 A1 | 12/2007 | Goldfarb et al. |
| 2007/0293946 A1 | 12/2007 | Gonzales et al. |
| 2008/0004613 A1 | 1/2008 | Barbut et al. |
| 2008/0015472 A1 | 1/2008 | Ressemann et al. |
| 2008/0015540 A1 | 1/2008 | Muni et al. |
| 2008/0082045 A1 | 4/2008 | Goldfarb et al. |
| 2008/0097154 A1 | 4/2008 | Makower et al. |
| 2008/0097239 A1 | 4/2008 | Chang et al. |
| 2008/0097295 A1 | 4/2008 | Makower et al. |
| 2008/0097400 A1 | 4/2008 | Chang et al. |
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0103361 A1 | 5/2008 | Makower et al. |
| 2008/0103521 A1 | 5/2008 | Makower et al. |
| 2008/0119693 A1 | 5/2008 | Makower et al. |
| 2008/0125626 A1 | 5/2008 | Chang et al. |
| 2008/0125720 A1 | 5/2008 | Kim et al. |
| 2008/0132938 A1 | 6/2008 | Chang et al. |
| 2008/0154237 A1 | 6/2008 | Chang et al. |
| 2008/0154250 A1 | 6/2008 | Makower et al. |
| 2008/0172033 A1 | 7/2008 | Keith et al. |
| 2008/0183128 A1 | 7/2008 | Morriss et al. |
| 2008/0195041 A1 | 8/2008 | Goldfarb et al. |
| 2008/0208242 A1 | 8/2008 | Becker |
| 2008/0208243 A1 | 8/2008 | Becker |
| 2008/0215082 A1 | 9/2008 | Becker |
| 2008/0215083 A1 | 9/2008 | Becker |
| 2008/0228085 A1 | 9/2008 | Jenkins et al. |
| 2008/0234720 A1 | 9/2008 | Chang et al. |
| 2008/0243140 A1 | 10/2008 | Gopferich et al. |
| 2008/0262468 A1 | 10/2008 | Clifford et al. |
| 2008/0262505 A1 | 10/2008 | Shahoian |
| 2008/0262508 A1 | 10/2008 | Clifford et al. |
| 2008/0262509 A1 | 10/2008 | Clifford et al. |
| 2008/0262510 A1 | 10/2008 | Clifford |
| 2008/0269643 A1 | 10/2008 | Morriss |
| 2008/0275483 A1 | 11/2008 | Makower et al. |
| 2008/0279895 A1 | 11/2008 | Blumenfeld |
| 2008/0281156 A1 | 11/2008 | Makower et al. |
| 2008/0281300 A1 | 11/2008 | Morriss |
| 2008/0281349 A2 | 11/2008 | Becker |
| 2008/0287908 A1 | 11/2008 | Muni et al. |
| 2008/0293999 A1 | 11/2008 | Halahmi |
| 2008/0319424 A1 | 12/2008 | Muni et al. |
| 2009/0005763 A1 | 1/2009 | Makower et al. |
| 2009/0028923 A1 | 1/2009 | Muni et al. |
| 2009/0030274 A1 | 1/2009 | Goldfarb et al. |
| 2009/0054803 A1 | 2/2009 | Saadat et al. |
| 2009/0076331 A1 | 3/2009 | Konwitz et al. |
| 2009/0093823 A1 | 4/2009 | Chang et al. |
| 2009/0125046 A1 | 5/2009 | Becker |
| 2009/0156980 A1 | 6/2009 | Eaton et al. |
| 2009/0163848 A1 | 6/2009 | Morriss et al. |
| 2009/0163890 A1 | 6/2009 | Clifford et al. |
| 2009/0171301 A1 | 7/2009 | Becker |
| 2009/0181074 A1 | 7/2009 | Makower et al. |
| 2009/0187098 A1 | 7/2009 | Makower et al. |
| 2009/0198216 A1 | 8/2009 | Muni et al. |
| 2009/0214466 A1 | 8/2009 | Levin |
| 2009/0227900 A1 | 9/2009 | Kim et al. |
| 2009/0240112 A1 | 9/2009 | Goldfarb et al. |
| 2009/0240237 A1 | 9/2009 | Goldfarb et al. |
| 2009/0304802 A1 | 12/2009 | Djupesland et al. |
| 2009/0306588 A1 | 12/2009 | Nguyen et al. |
| 2009/0312696 A1 | 12/2009 | Copa et al. |
| 2009/0312745 A1 | 12/2009 | Goldfarb et al. |
| 2009/0318797 A1 | 12/2009 | Hadani |
| 2010/0010302 A1 | 1/2010 | Hadani |
| 2010/0016844 A1 | 1/2010 | Patel et al. |
| 2010/0030031 A1 | 2/2010 | Goldfarb et al. |
| 2010/0030113 A1 | 2/2010 | Morriss et al. |
| 2010/0030131 A1 | 2/2010 | Morriss et al. |
| 2010/0030187 A1 | 2/2010 | Xia |
| 2010/0030188 A1 | 2/2010 | Xia |
| 2010/0035805 A1 | 2/2010 | Hafner |
| 2010/0042046 A1 | 2/2010 | Chang et al. |
| 2010/0056867 A1 | 3/2010 | LaBombard et al. |
| 2010/0057048 A1 | 3/2010 | Eldredge |
| 2010/0076269 A1 | 3/2010 | Makower et al. |
| 2010/0081873 A1 | 4/2010 | Tanimura et al. |
| 2010/0099946 A1 | 4/2010 | Jenkins et al. |
| 2010/0100181 A1 | 4/2010 | Makower et al. |
| 2010/0105983 A1 | 4/2010 | Oneda et al. |
| 2010/0114066 A1 | 5/2010 | Makower et al. |
| 2010/0114184 A1 | 5/2010 | Degtyar et al. |
| 2010/0121308 A1 | 5/2010 | Muni et al. |
| 2010/0152730 A1 | 6/2010 | Makower et al. |
| 2010/0168511 A1 | 7/2010 | Muni et al. |
| 2010/0174138 A1 | 7/2010 | Chang et al. |
| 2010/0174196 A1 | 7/2010 | Ryan et al. |
| 2010/0174308 A1 | 7/2010 | Chang et al. |
| 2010/0179488 A1 | 7/2010 | Spiegel et al. |
| 2010/0179511 A1 | 7/2010 | Rajan et al. |
| 2010/0198135 A1 | 8/2010 | Morriss et al. |
| 2010/0198191 A1 | 8/2010 | Clifford et al. |
| 2010/0198247 A1 | 8/2010 | Chang et al. |
| 2010/0210901 A1 | 8/2010 | Makower et al. |
| 2010/0211005 A1 | 8/2010 | Edwards et al. |
| 2010/0211007 A1 | 8/2010 | Lesch et al. |
| 2010/0211140 A1 | 8/2010 | Barbut et al. |
| 2010/0217296 A1 | 8/2010 | Morriss et al. |
| 2010/0241068 A1 | 9/2010 | Chen |
| 2010/0241155 A1 | 9/2010 | Chang et al. |
| 2010/0256653 A1 | 10/2010 | Kaplan et al. |
| 2010/0268245 A1 | 10/2010 | Chang et al. |
| 2010/0274188 A1 | 10/2010 | Chang et al. |
| 2010/0274222 A1 | 10/2010 | Setliff et al. |
| 2010/0280626 A1 | 11/2010 | Shalon et al. |
| 2010/0282246 A1 | 11/2010 | Djupesland et al. |
| 2010/0286659 A1 | 11/2010 | Terrill et al. |
| 2010/0292765 A1 | 11/2010 | Etwil |
| 2010/0298640 A1 | 11/2010 | Oneda et al. |
| 2010/0298862 A1 | 11/2010 | Chang et al. |
| 2010/0305697 A1 | 12/2010 | Clifford et al. |
| 2010/0324483 A1 | 12/2010 | Rozenberg et al. |
| 2011/0004057 A1 | 1/2011 | Goldfarb et al. |
| 2011/0004058 A1 | 1/2011 | Oneda et al. |
| 2011/0004192 A1 | 1/2011 | Eaton et al. |
| 2011/0004194 A1 | 1/2011 | Eaton et al. |
| 2011/0015645 A1 | 1/2011 | Liu et al. |
| 2011/0015734 A1 | 1/2011 | Gonzales et al. |
| 2011/0020279 A1 | 1/2011 | Shantha |
| 2011/0054395 A1 | 3/2011 | O'Dea et al. |
| 2011/0060214 A1 | 3/2011 | Makower |
| 2011/0087192 A1 | 4/2011 | Uhland et al. |
| 2011/0098659 A1 | 4/2011 | Covello |
| 2011/0112512 A1 | 5/2011 | Muni et al. |
| 2011/0114087 A1 | 5/2011 | Djupesland et al. |
| 2011/0152838 A1 | 6/2011 | Xia |
| 2011/0160623 A1 | 6/2011 | Shalev |
| 2011/0160740 A1 | 6/2011 | Makower et al. |
| 2011/0208215 A1 | 8/2011 | Modesitt et al. |
| 2011/0224652 A1 | 9/2011 | Drontle et al. |
| 2011/0245765 A1 | 10/2011 | Jacobsen et al. |
| 2011/0288559 A1 | 11/2011 | Shahoian |
| 2011/0318345 A1 | 12/2011 | Djupesland |
| 2012/0010646 A1 | 1/2012 | Keith et al. |
| 2012/0017893 A1 | 1/2012 | Xia |
| 2012/0046607 A1 | 2/2012 | Syk |
| 2012/0053404 A1 | 3/2012 | Schreck et al. |
| 2012/0071715 A1 | 3/2012 | Beyar et al. |
| 2012/0071727 A1 | 3/2012 | Hanson et al. |
| 2012/0071824 A1 | 3/2012 | Chang et al. |
| 2012/0071856 A1 | 3/2012 | Goldfarb et al. |
| 2012/0071857 A1 | 3/2012 | Goldfarb et al. |
| 2012/0078118 A1 | 3/2012 | Jenkins et al. |
| 2012/0078377 A1 | 3/2012 | Gonzales et al. |
| 2012/0089028 A1 | 4/2012 | Hadani et al. |
| 2012/0090620 A1 | 4/2012 | Deutsch |
| 2012/0101343 A1 | 4/2012 | Duffy et al. |
| 2012/0116254 A1 | 5/2012 | Morriss |
| 2012/0128683 A1 | 5/2012 | Shantha |
| 2012/0136207 A1 | 5/2012 | Goldfarb et al. |

(56) References Cited

U.S. PATENT DOCUMENTS

| | | |
|---|---|---|
| 2012/0157968 A1 | 6/2012 | Eldredge et al. |
| 2012/0172751 A1 | 7/2012 | Levin |
| 2012/0172835 A1 | 7/2012 | Becker |
| 2012/0184983 A1 | 7/2012 | Chang et al. |
| 2012/0220923 A1 | 8/2012 | Morriss et al. |
| 2012/0221034 A1 | 8/2012 | Dinger et al. |
| 2012/0227457 A1 | 9/2012 | Kim et al. |
| 2012/0245419 A1 | 9/2012 | Makower et al. |
| 2012/0245456 A1 | 9/2012 | Kim et al. |
| 2012/0259215 A1 | 10/2012 | Gerrans et al. |
| 2012/0259216 A1 | 10/2012 | Gerrans et al. |
| 2012/0265094 A1 | 10/2012 | Goldfarb et al. |
| 2012/0277578 A1 | 11/2012 | Gunday et al. |
| 2012/0302825 A1 | 11/2012 | Schaeffer et al. |
| 2012/0310145 A1 | 12/2012 | Clifford et al. |
| 2012/0323214 A1 | 12/2012 | Shantha |
| 2013/0006055 A1 | 1/2013 | Goldfarb et al. |
| 2013/0018431 A1 | 1/2013 | Levin |
| 2013/0030458 A1 | 1/2013 | Drontle et al. |
| 2013/0041463 A1 | 2/2013 | Ressemann |
| 2013/0053644 A1 | 2/2013 | Smith et al. |
| 2013/0053822 A1 | 2/2013 | Fischell et al. |
| 2013/0053824 A1 | 2/2013 | Seiden et al. |
| 2013/0066358 A1 | 3/2013 | Nalluri et al. |
| 2013/0072958 A1 | 3/2013 | Ressemann et al. |
| 2013/0073015 A1 | 3/2013 | Rozenberg |
| 2013/0085472 A1 | 4/2013 | Shaari |
| 2013/0090544 A1 | 4/2013 | Clifford et al. |
| 2013/0096605 A1 | 4/2013 | Becker |
| 2013/0103023 A1 | 4/2013 | Monson et al. |
| 2013/0123833 A1 | 5/2013 | Lesch et al. |
| 2013/0130145 A1 | 5/2013 | Kaeding et al. |
| 2013/0158475 A1 | 6/2013 | Xia et al. |
| 2013/0165873 A1 | 6/2013 | Morriss et al. |
| 2013/0172852 A1 | 7/2013 | Chang |
| 2013/0184532 A1 | 7/2013 | Goldfarb et al. |
| 2013/0184568 A1 | 7/2013 | Muni et al. |
| 2013/0184574 A1 | 7/2013 | Newhauser et al. |
| 2013/0184683 A1 | 7/2013 | Chow et al. |
| 2013/0190678 A1 | 7/2013 | Andreas et al. |
| 2013/0197426 A1 | 8/2013 | Morriss et al. |
| 2013/0231529 A1 | 9/2013 | John et al. |
| 2013/0245608 A1 | 9/2013 | Muni et al. |
| 2013/0245609 A1 | 9/2013 | Schaeffer et al. |
| 2013/0261388 A1 | 10/2013 | Jenkins et al. |
| 2013/0274600 A1 | 10/2013 | Jenkins et al. |
| 2013/0274651 A1 | 10/2013 | Barbut et al. |
| 2013/0274715 A1 | 10/2013 | Chan et al. |
| 2013/0276794 A1 | 10/2013 | Morriss |
| 2013/0281982 A1 | 10/2013 | Makower et al. |
| 2013/0302445 A1 | 11/2013 | Barbut et al. |
| 2013/0303968 A1 | 11/2013 | Clifford et al. |
| 2013/0324970 A1 | 12/2013 | Arcand et al. |
| 2013/0325052 A1 | 12/2013 | Chang et al. |
| 2014/0012182 A1 | 1/2014 | Shantha |
| 2014/0018775 A1 | 1/2014 | Swords et al. |
| 2014/0030520 A1 | 1/2014 | Nakamura et al. |
| 2014/0031726 A1 | 1/2014 | Chernomorsky et al. |
| 2014/0031792 A1 | 1/2014 | Darin et al. |
| 2014/0066901 A1 | 3/2014 | Dinger et al. |
| 2014/0066928 A1 | 3/2014 | Bennett et al. |
| 2014/0073858 A1 | 3/2014 | Sherwinter |
| 2014/0074065 A1 | 3/2014 | Muni et al. |
| 2014/0074140 A1 | 3/2014 | Johnson et al. |
| 2014/0074141 A1 | 3/2014 | Johnson et al. |
| 2014/0088498 A1 | 3/2014 | Stevens et al. |
| 2014/0094733 A1 | 4/2014 | Clopp et al. |
| 2014/0107404 A1 | 4/2014 | Gruber |
| 2014/0107427 A1 | 4/2014 | Chow et al. |
| 2014/0114233 A1 | 4/2014 | Deem et al. |
| 2014/0135587 A1 | 5/2014 | Hess |
| 2014/0144443 A1 | 5/2014 | Djupesland et al. |
| 2014/0163072 A1 | 6/2014 | Romon-de-Jesus |
| 2014/0180328 A1 | 6/2014 | Vaccaro et al. |
| 2014/0200443 A1 | 7/2014 | Chang et al. |
| 2014/0200444 A1 | 7/2014 | Kim et al. |
| 2014/0213968 A1 | 7/2014 | Vaccaro et al. |
| 2014/0218904 A1 | 8/2014 | Cayton |
| 2014/0238398 A1 | 8/2014 | Christopher et al. |
| 2014/0242064 A1 | 8/2014 | Morriss et al. |
| 2014/0243792 A1 | 8/2014 | Berman et al. |
| 2014/0243793 A1 | 8/2014 | Morriss et al. |
| 2014/0243876 A1 | 8/2014 | Suehara |
| 2014/0276624 A1 | 9/2014 | Jeppson |
| 2014/0276626 A1 | 9/2014 | Jenkins et al. |
| 2014/0276627 A1 | 9/2014 | Jenkins et al. |
| 2014/0277072 A1 | 9/2014 | Suehara |
| 2014/0288623 A1 | 9/2014 | Levin |
| 2014/0295728 A1 | 10/2014 | Cayton |
| 2014/0296898 A1 | 10/2014 | Chang et al. |
| 2014/0324093 A1 | 10/2014 | Chang et al. |
| 2014/0330074 A1 | 11/2014 | Morriss et al. |
| 2014/0336575 A1 | 11/2014 | Muni et al. |
| 2014/0336693 A1 | 11/2014 | Goldfarb et al. |
| 2014/0336694 A1 | 11/2014 | Becker |
| 2014/0350520 A1 | 11/2014 | Drontle et al. |
| 2015/0038901 A1 | 2/2015 | Lampropoulos et al. |
| 2015/0039014 A1 | 2/2015 | Schaeffer et al. |
| 2015/0045825 A1 | 2/2015 | Caplan et al. |
| 2015/0065872 A1 | 3/2015 | Drake et al. |
| 2015/0065995 A1 | 3/2015 | Sanchez et al. |
| 2015/0141819 A1 | 5/2015 | Linden et al. |
| 2015/0141915 A1 | 5/2015 | Lampropoulos et al. |
| 2015/0164309 A1 | 6/2015 | Chandler et al. |
| 2015/0164571 A1 | 6/2015 | Saadat |
| 2015/0173592 A1 | 6/2015 | Leeflang et al. |
| 2015/0174406 A1 | 6/2015 | Lamensdorf et al. |
| 2015/0196735 A1 | 7/2015 | Olig et al. |
| 2015/0196753 A1 | 7/2015 | Levin |
| 2015/0230700 A1 | 9/2015 | Chandler et al. |
| 2015/0258315 A1 | 9/2015 | Chandler et al. |
| 2015/0352341 A1 | 12/2015 | Chandler et al. |
| 2016/0008017 A1 | 1/2016 | Makower et al. |
| 2016/0135671 A1 | 5/2016 | Chandler et al. |
| 2016/0271375 A1 | 9/2016 | Chandler et al. |
| 2017/0246434 A1 | 8/2017 | Chandler et al. |
| 2018/0042471 A1 | 2/2018 | Chandler et al. |
| 2018/0333564 A1 | 11/2018 | Chandler et al. |
| 2019/0091450 A1 | 3/2019 | Chandler et al. |

FOREIGN PATENT DOCUMENTS

| | | | |
|---|---|---|---|
| EP | 2522586 A2 | 11/2012 | |
| EP | 1 988 953 B1 | 7/2017 | |
| GB | 2 397 025 A | 7/2004 | |
| GB | 2 397 243 A | 7/2004 | |
| GB | 2 402 886 A | 12/2004 | |
| GB | 2 403 154 A | 12/2004 | |
| GB | 2 404 867 A | 2/2005 | |
| GB | 2 405 350 A | 3/2005 | |
| GB | 2 405 800 A | 3/2005 | |
| GB | 2 414 414 A | 11/2005 | |
| KR | 20050117277 A | 12/2005 | |
| KR | 1020050117277 A | 4/2006 | |
| KR | 1020120013930 A | 2/2012 | |
| WO | 2002005703 A1 | 1/2002 | |
| WO | 2002007632 A1 | 1/2002 | |
| WO | 2006020180 A2 | 2/2006 | |
| WO | 2010078145 A1 | 7/2010 | |
| WO | 2012/123819 A1 | 9/2012 | |
| WO | 2015/095214 A1 | 6/2015 | |
| WO | 2015095214 A1 | 6/2015 | |
| WO | WO-2016108055 A2 * | 7/2016 | ........... A61K 9/0075 |

OTHER PUBLICATIONS

Borris, et al., "Intraoperative nasal transillumination for maxillary sinus augmentation procedures: A technical note," International Journal of Oral and Maxillofacial Implants, vol. 13, Issue 4 (Jul.-Aug. 1998), pp. 569-570 (abstract only).

Friedman, et al., "Intraoperative and Postoperative Assessment of Frontal Sinus Patency by Transillumination," The Laryngoscope, vol. 110 (Apr. 2000), pp. 683-684.

(56) References Cited

OTHER PUBLICATIONS

Hung, et al., "Lightwand intubation: II—Clinical trial of a new lightwand for tracheal intubation in patients with difficult airways," Canadian Journal of Anaesthesia, vol. 42, Issue 9 (1995), pp. 826-830.
Massengill, "An Objective Technique for Submucous Cleft Palate Detection," Plastic and Reconstructive Surgery, vol. 37, No. 4 (1966), pp. 355-359.
Miyazaki, et al., "Fiberscopic Methods for Assessment of Velopharyngeal Closure during Various Activities," presented at the 15th annual convention of the Japan Society of Oral Surgery in Nagoya, Oct. 1970; presented at the 25th annual convention of the Japan Society of Oral Medicine in Tokyo, Apr. 1971; and presented at the 2nd International Cleft Palate Congress in Copenhagen, Aug. 1973.
U.S. Appl. No. 14/298,521 entitled Method of Performing a Sphenopalatine Ganglion—Block Procedure, filed Jun. 6, 2014.
U.S. Appl. No. 14/572,353 entitled Surgical Device for Performing a Sphenopalatine Ganglion Block Procedure, filed Dec. 16, 2014.
U.S. Appl. No. 14/712,722 entitled Method of Performing a Sphenopalatine Ganglion Block Procedure, filed May 14, 2015.
U.S. Appl. No. 15/008,115 entitled Method of Performing a Sphenopalatine Ganglion Block Procedure, filed Jan. 27, 2016.
U.S. Appl. No. 29/512,059 entitled Surgical Device, filed Dec. 16, 2014, 2015.
International Preliminary Report on Patentability for International Application No. PCT/US2014/070642 dated Apr. 9, 2015—12 pages.
International Search Report (ISR) for International Application No. PCT/US2014/070642 dated Apr. 9, 2015—3 pages.
Written Opinion of the International Searching Authority for International Application No. PCT/US2014/070642 dated Apr. 9, 2015—11 pages.
Cohen, et. al., "Transnasal Illumination to Guide the Craniofacial Resection of Anterior Skull Based Neoplasms," Surgical Neurology, vol. 40 (1993), pp. 420-423.
Dolor, et. al., "Management of Rhinosinusitis in Adults: Clinical Applications of Recent Evidence and Treatment Recommendations," Journal of Clinical Outcomes Management, vol. 9, No. 8 (Aug. 2002), pp. 463-476.
Felisati, "Headache & Migraine; Sphenopalatine endoscopic ganglion block alleviates cluster headache symptoms," Life Science Weekly (Oct. 10, 2006), pp. 741.
Petroianu, et. al., "Intubation with Transillumination: Nasal or Oral?" Prehospital and Disaster Medicine, vol. 14, No. 2 (Apr.-Jun. 1999), pp. 72-73.
WelchAllyn Pocketscopes, Operating Instruction Manual, circa 2000.
WelchAllyn 3.5v Transilluminators product brochure, circa 2000.

\* cited by examiner

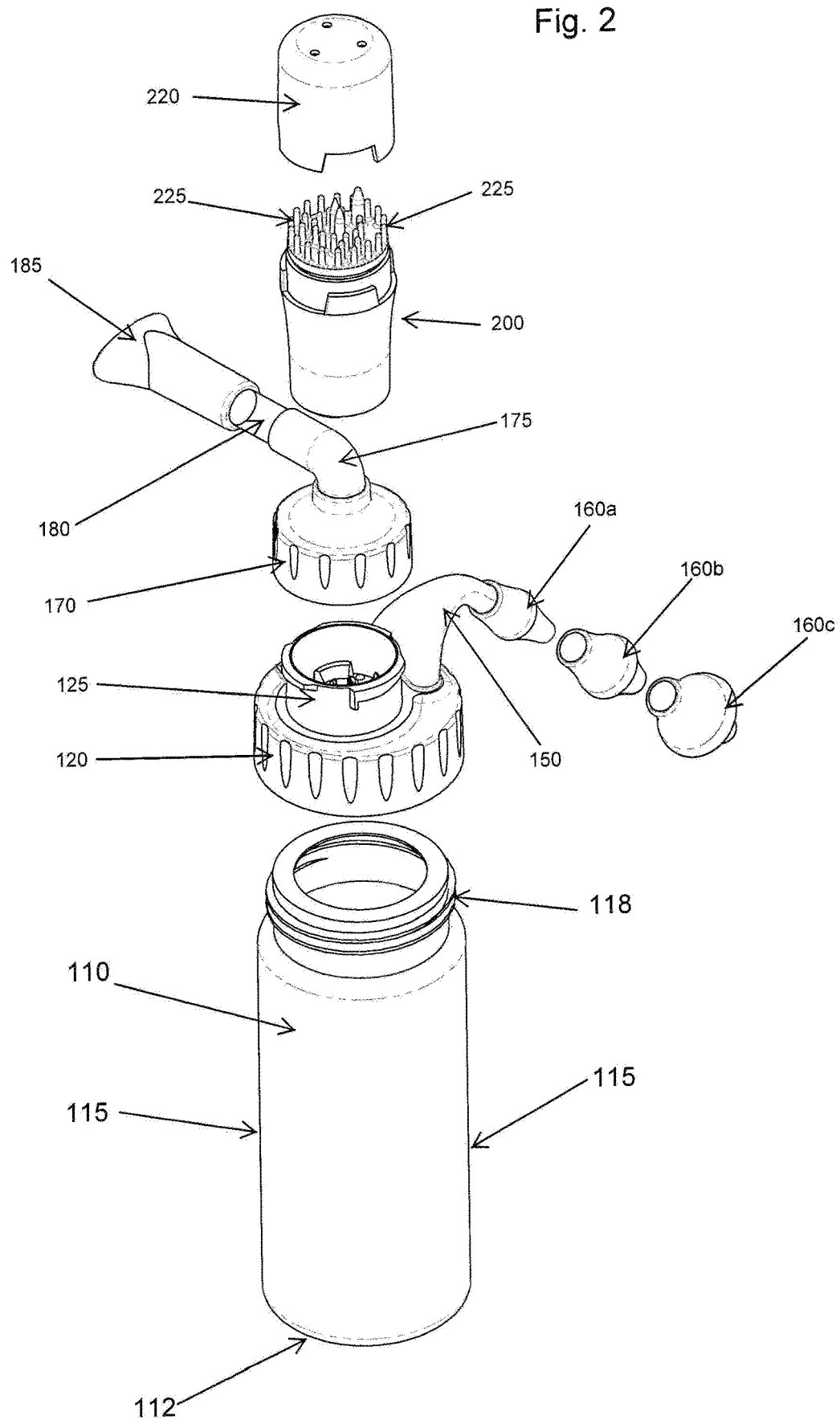

SINO-NASAL RINSE DELIVERY DEVICE WITH AGITATION, FLOW-CONTROL AND INTEGRATED MEDICATION MANAGEMENT SYSTEM

CROSS REFERENCE TO RELATED APPLICATION

The present application claims the benefit of and priority to, under 35 U.S.C. § 119(e), U.S. Provisional Application Ser. No. 62/691,010 filed on Jun. 28, 2018 entitled "Sino-Nasal Rinse Delivery Device with Agitation, Flow-Control and Integrated Medication Management System"; U.S. Provisional Application Ser. No. 62/782,889 filed on Dec. 20, 2018 entitled "Sino-Nasal Apparatus and Delivery Method Using Choanal Blockade and Electronic Agent Vaporization"; and, U.S. Provisional Application Ser. No. 62/782,898 filed on Dec. 20, 2018 entitled "Eustachian Tube Dysfunction Treatment Method with Isolating, Incremental, Auto-Insufflation Pressure Generator", which are hereby incorporated herein by reference in their entireties for all that they teach and for all purposes.

TECHNICAL FIELD

Embodiments of the present disclosure relate to nasal and sinus devices. More specifically, embodiments of the disclosure relate to delivering an solution/substance to the nasal and sinus cavities.

BACKGROUND

Paranasal sinuses are cavities formed within the bones of the face that are accessible via an individual's nasal cavity. The paranasal sinuses include the frontal sinuses, the sphenoid sinuses, the ethmoid sinuses, and the maxillary sinuses. Sino-nasal anatomy includes bilateral inferior, middle and supreme turbinate and the midline nasal septum. The paranasal sinuses and nose are lined with mucous-producing respiratory epithelial tissue.

Normally, mucous produced by the linings of the sino-nasal sinuses slowly drains out of each sinus through an opening known as an ostium. Some conditions, however, can interfere with the drainage of the mucous. A healthy sino-nasal condition depends upon proper mucous drainage from the sinus cavities and the nose. When this natural process is disrupted by the effects of allergen, other bioactive particulate matter deposits or abnormal anatomic variations a condition of mucous stasis in the sinus cavities or the nose. As a consequence, nasal lining mucositis and/or sino-nasal disorders (e.g., a sinus infection, sinus headache, epistaxis, nasal obstruction, rhinorrhea) can result. Some of the conventional systemic approaches to treating these disorders often result in cutaneous rash, diarrhea, bacterial resistance from antibiotic use, adrenal suppression, weight gain from steroid medications, hypertension, sleep disturbance from decongestant use, epistaxis, headache, vertigo and others.

Surgery that is performed on the paranasal sinus cavities results in altered, modified or otherwise widened sinus drainage pathways compared to native outflow tracts.

Direct application of a substance to a sinus through a nasal cavity may avoid some of the side-effects listed above that are inherent in a systemic approach to treating sinusitis, rhinitis and/or mucositis.

However, due to the lateral or superior location of sinus outflow tracts the introduction of a substance via a trans-nasal route may result in a large majority of the substance bypassing the intended sinus cavity ostia.

More specifically, the post-surgical maxillary sinus ostia is located on the lateral nasal wall approximately 3.0 to 4.0 centimeters from the apex of the external nasal vestibule and approximately at a 45 degree angle with respect to the floor of the nose. Thus, a substance delivered using a device introduced into the nose at approximately 45 degrees from the floor of the nose with an approximate length of 3 to 4 centimeters and with the capability of directing a substance at an 80 to 90 degree angle relative to the device itself would have the capability of directly delivering a substance to the maxillary sinus cavity when properly oriented.

Additionally, the post-surgical frontal sinus outflow tract is located superiorly in the nasal cavity at approximately 5 to 6 centimeters from the apex of the external nasal vestibule at approximately 75° to 85° relative to the floor of the nose. Thus, a substance delivered using a device introduced into the nose at approximately 45 degrees from the floor of the nose with an approximate length of 3 to 4 centimeters and with the capability of directing a substance at an 80 to 90 degree angle relative to the device itself would have the capability of directly delivering a substance to the frontal sinus cavity when properly oriented.

Accordingly, there is a need for a device, system, and method of treatment that has the capability to quickly and accurately apply a substance directly to a laterally or superiorly located paranasal sinus outflow tract. The present disclosure discusses a device that satisfies such needs, among the others delineated.

Direct application of a substance to an infected sinus through a nasal cavity will avoid some of the side-effects listed above that are inherent in a systemic approach. However, the introduction of a substance via a trans-nasal route may result in a large majority of the substance flowing down the individual's throat, resulting in possible aspiration, coughing and or choking; if the substance enters the oral cavity it also is distasteful, which further exacerbates the unpleasantness. Additionally, if a substance is forcibly introduced into a nasal cavity it is possible to overcome physiologic proximal Eustachian tube resistance resulting in the substance contaminating the middle-ear. The presence of a substance (other than physiologic body-temperature aeration) in the middle-ear may result in aural fullness, otitis effusion, otitis media, hearing loss (possibly permanent), ossicular chain injury, damage to the middle-ear mucosal lining, dizziness/unsteadiness, nystagmus, nausea and others.

Accordingly, there is a need for a device and/or system that has the capability to quickly and accurately apply a substance to a paranasal sinus and/or sino-nasal cavity, prevent the substance applied to a paranasal sinus and/or sino-nasal cavity from flowing down a patient's throat and/or prevent the substance from contaminating the middle-ear cavity. The present disclosure discusses a device that satisfies such needs, among the others delineated.

Agents used in medicated sinus lavage are commonly supplied in capsule or other form; many individuals with dexterity problems are unable to manage the delivery of medication supplied in capsule or other form into sinus irrigation solution.

With respect to solubility of agents administered as a sinus lavage, there exist a category of agents that are immiscible in an aqueous or saline environment therefore presenting a challenge to delivery of a consistent agent concentration.

The use of saline or other sino-nasal irrigation solution delivered in a non-linear, turbulent, or pulsatile manner provides potentially additional cleansing properties over a solution delivered as a constant, uniform stream.

The effective use of gravity-assist sino-nasal lavage can be limited by an inability to control the flow of irrigation solution due to the siphon effect, i.e. a tube used to convey liquid upwards from a reservoir and then flows down to a lower level due to gravity, once the liquid has been forced into the tube and elevated, flow continues unaided and cannot easily be controlled or stopped.

The effective use of gravity-assist sino-nasal lavage can be further limited by an inability to extend the neck and look upwards, as is required in the application of conventional sino-nasal irrigation systems that rely on gravity to dispense the solution. This limitation is particularly acute for persons with neck extension limitations or persons who experience dizziness in this position, in particular elderly persons.

Sino-nasal rinsing can be limited by design features that are selective for specific anatomy, specifically that of adult versus children.

SUMMARY

Embodiments of the disclosure relate to delivering a pharmaceutically acceptable buffer preferably consisting of sterile saline solution or a solution with a therapeutically effective concentration of a pharmaceutical to nasal and sinus cavities. While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

The sino-nasal irrigation device consists of a reservoir container; a housing with a grinding chamber and nose piece; and an input apparatus with a mouth piece. The reservoir container is intended for holding an solution. The housing has a grinding chamber for crushing capsules, pills, and the like, with an integrated filter separating the grinding chamber and the reservoir container that allows ground material of a predetermined size to pass through the filter and into the reservoir container. The housing also has a nose piece with a nasal tip and an optional nasal tip extension.

When the sino-nasal irrigation device is assembled with a solution in the reservoir container, and inverted such that the reservoir container is above the input apparatus and the housing, the weight of the solution in the reservoir container pushes down on the diaphragm creating a negative pressure on the diaphragm. The weight of the solution on the diaphragm prevents air from entering the reservoir container and thus prevents solution from the reservoir container from flowing out through the nose piece. Applying a positive pressure to the bottom of the diaphragm causes the diaphragm to open and allows air to flow into the reservoir container. The air flowing into the reservoir container causes turbulence in the solution held in the reservoir container resulting in the mixing of the air and solution. The air flowing into the reservoir container also allows the solution in the reservoir container to flow out of the reservoir through the nose piece and into a user's nasal cavity. When the positive pressure on the bottom of the diaphragm is removed, the flow of liquid from the reservoir container stops.

DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 2 is an exploded perspective view of an illustrative system for delivering an solution to the nasal cavity or paranasal sinuses of a user, in accordance with the embodiments of the present disclosure.

DETAILED DESCRIPTION

Figure 1:
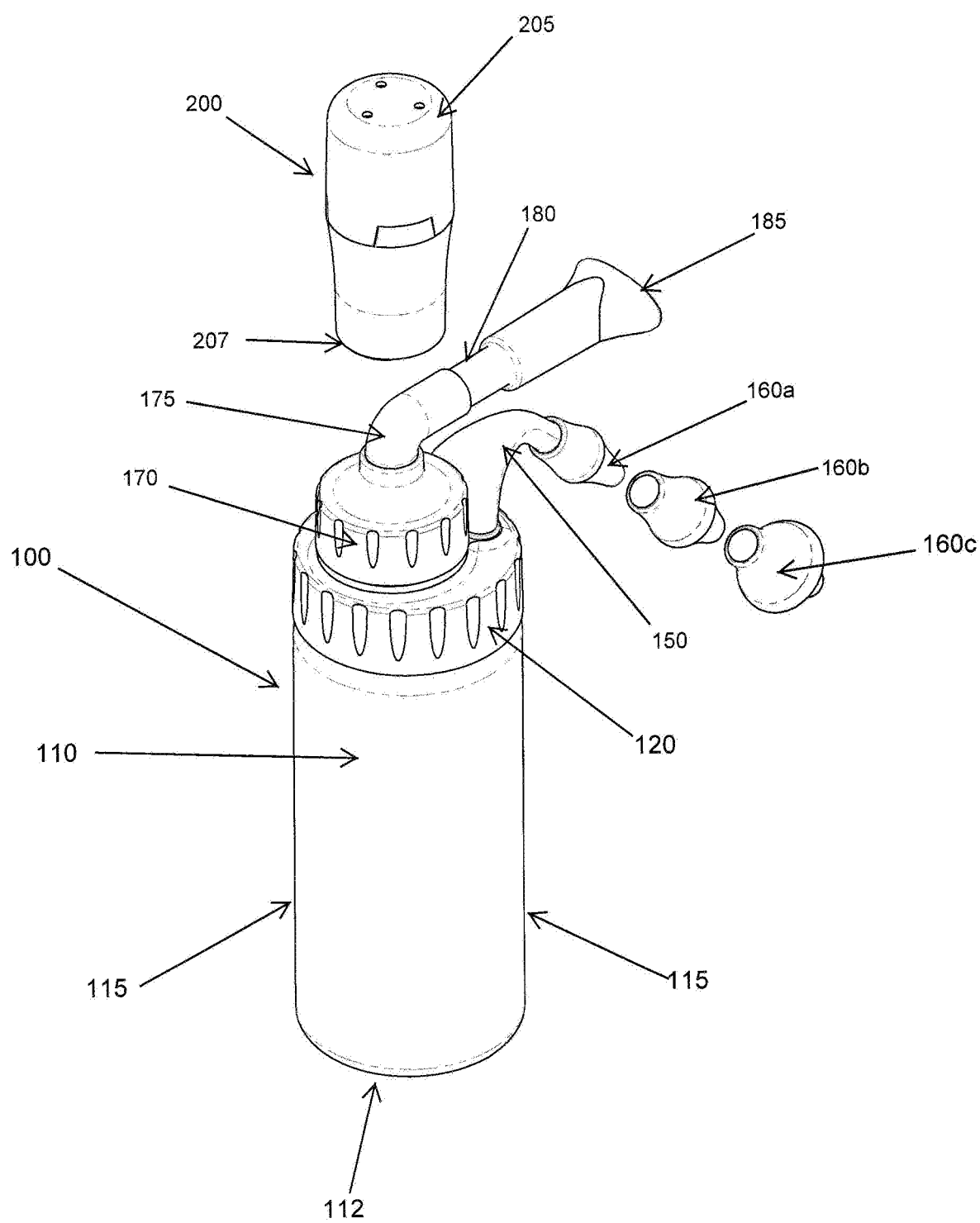
FIG. 1 is a perspective view of an illustrative system for delivering an solution to the nasal cavity and or paranasal sinuses of a user, in accordance with the embodiments of the present disclosure.
Figure 3A:
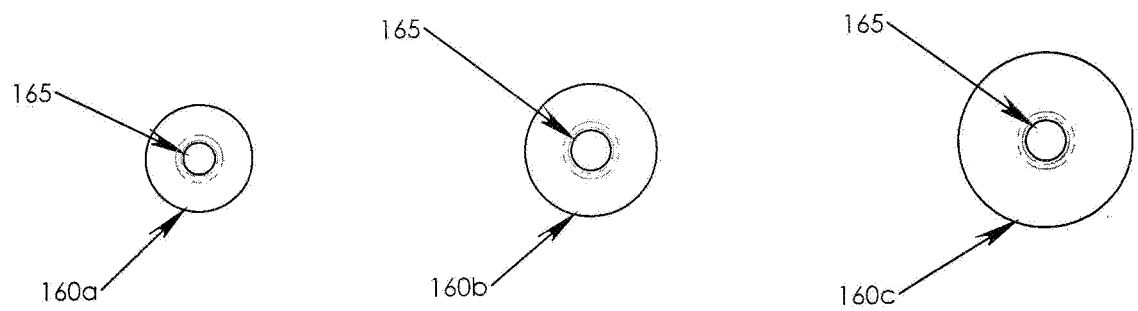
FIG. 3a is a top view of the nasal tips 160a to accommodate the customary nasal opening sizes of children, 160b adults generally, and 160c for larger adults.
Figure 3B:
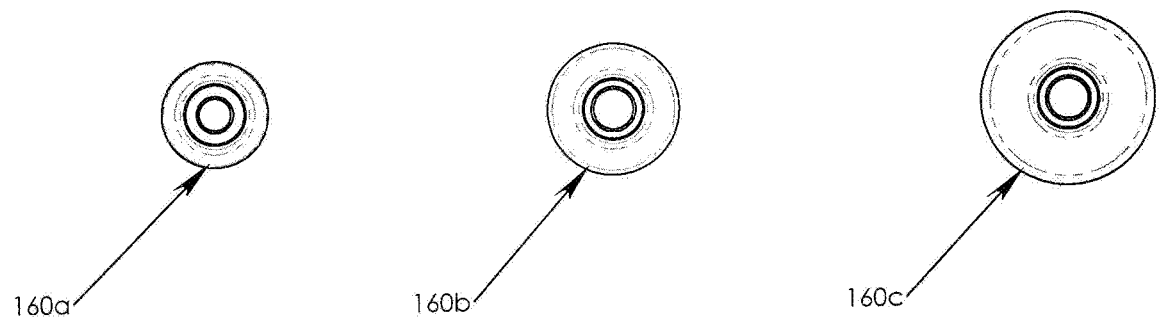
FIG. 3b is a bottom view of the nasal tips 160a to accommodate the customary nasal opening sizes of children, 160b adults generally, and 160c for larger adults.
Figure 3C:
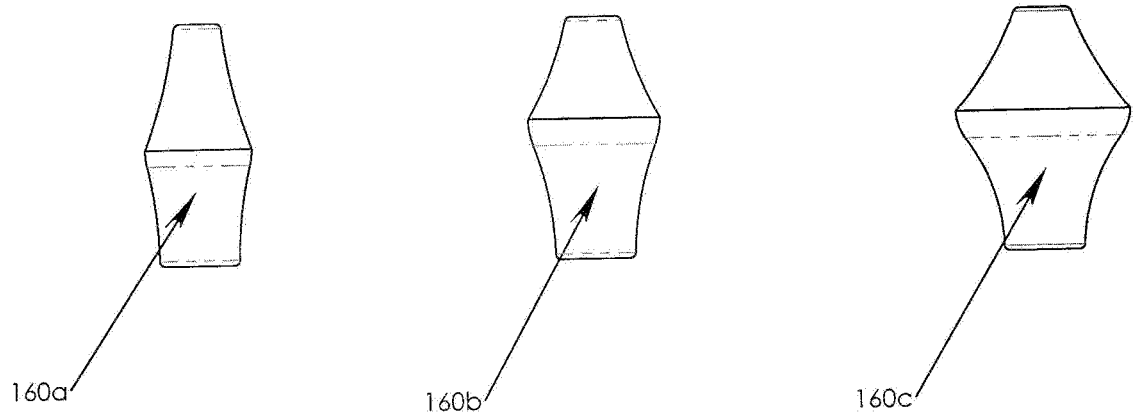
FIG. 3c is a sideview of the nasal tips 160a to accommodate the customary nasal opening sizes of children, 160b adults generally, and 160c for larger adults which are generally circular and thus the view from all sides is the same.
Figure 4:
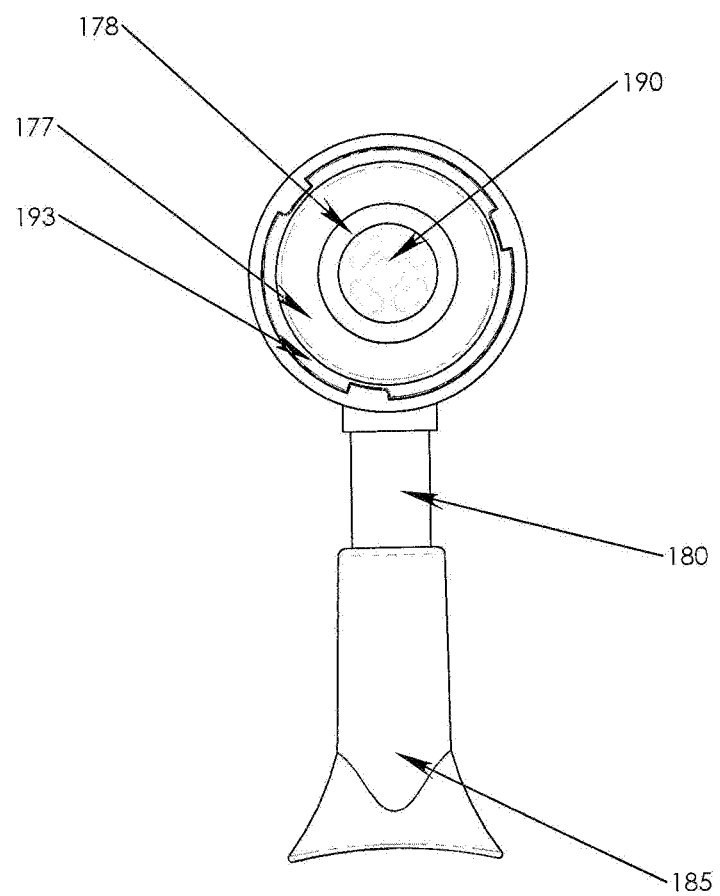
FIG. 4 is a bottom view of the input apparatus (170).
Figure 5A:
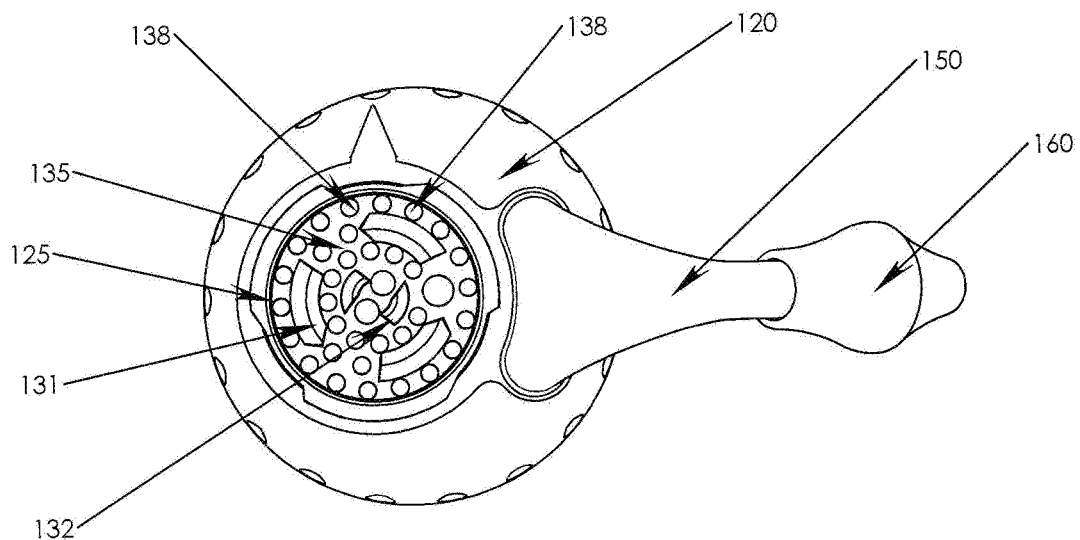
FIG. 5a is a top view of the housing (120).
Figure 5B:
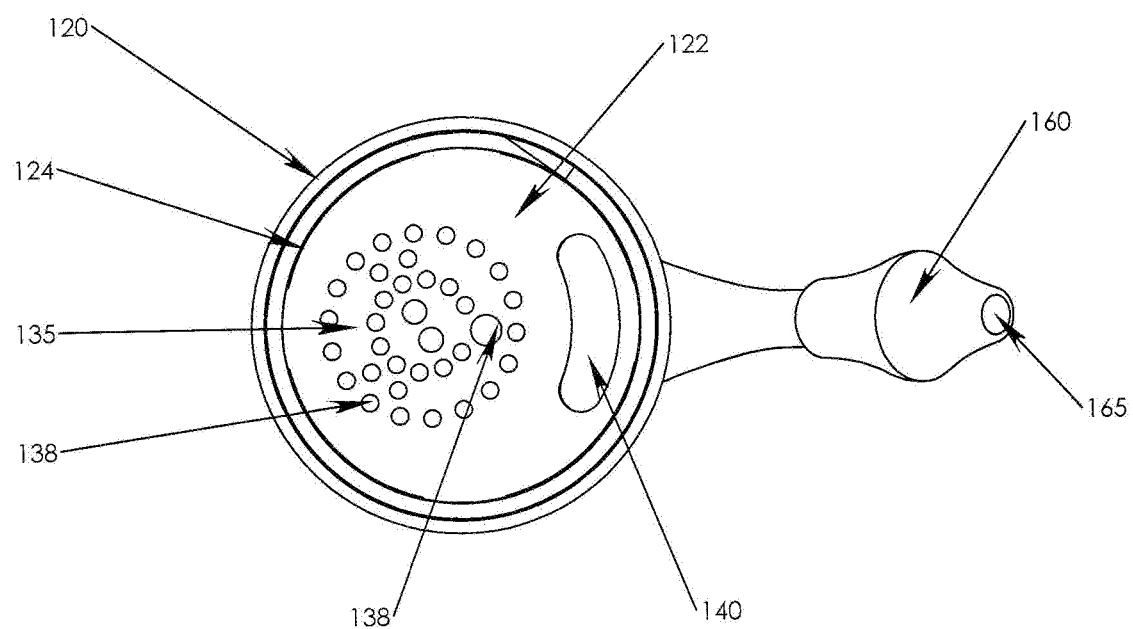
FIG. 5b is a bottom view of the housing (120).
Figure 6A:
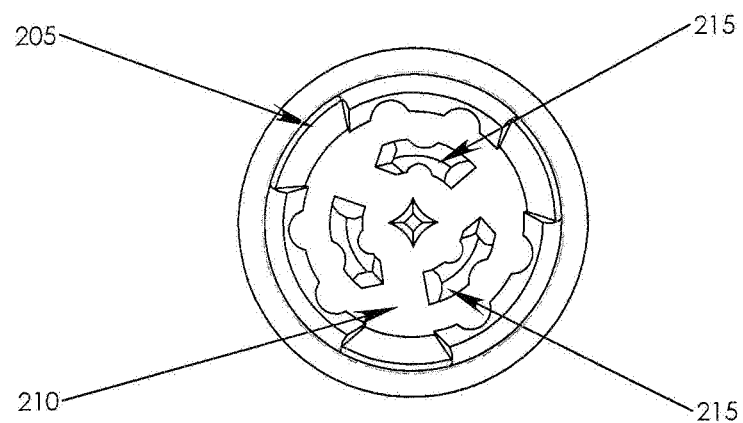
FIG. 6a is a view of the first distal end (205) of the mortar (200).
Figure 6B:
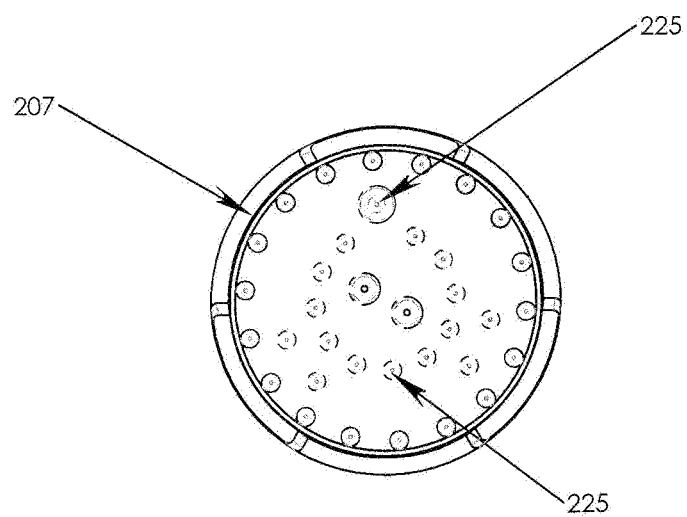
FIG. 6b is a view of the second distal end (207) of the mortar (200).
Figure 7:
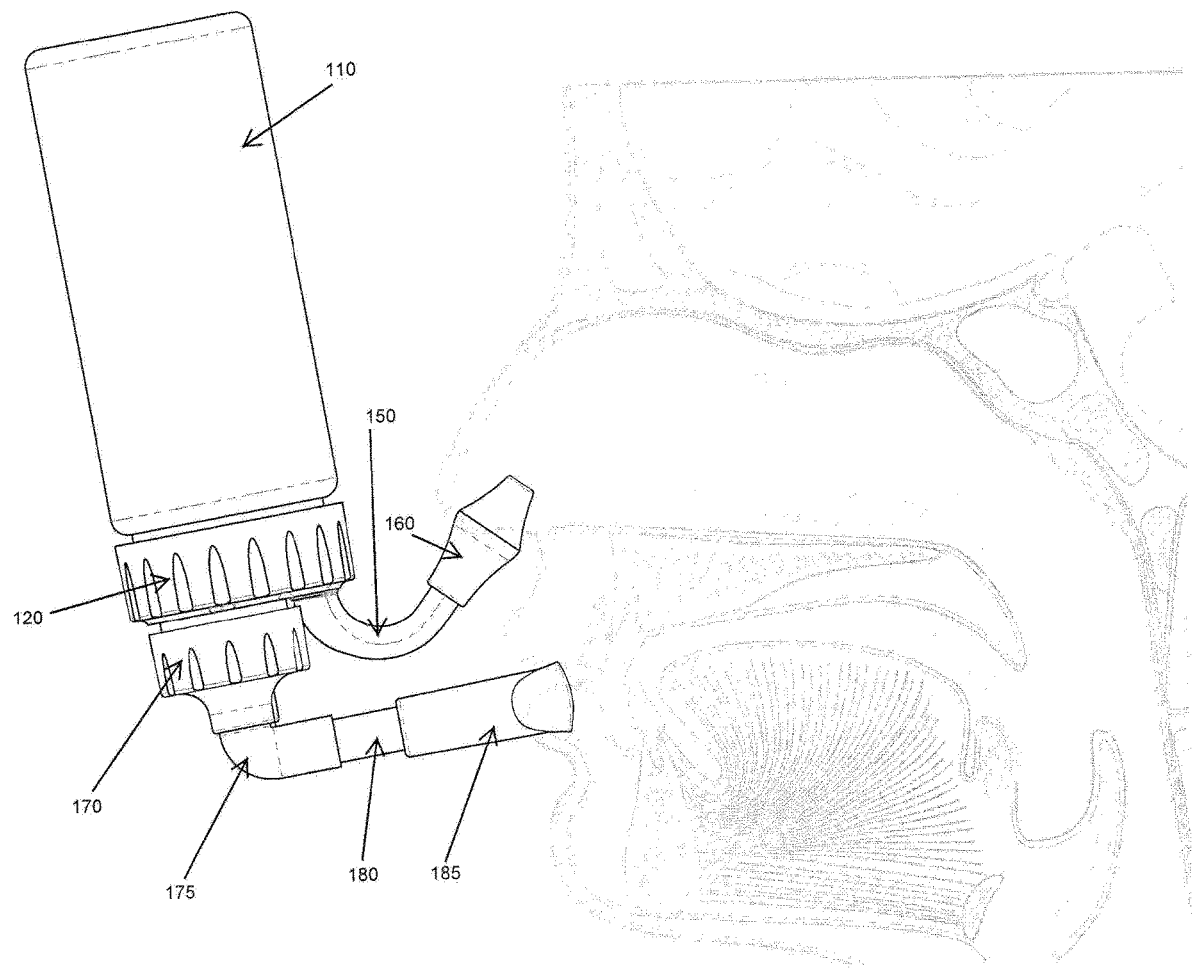
FIG. 7 is a cross-sectional view of a patient's head with an embodiment of the system for delivering an solution to the nasal cavity and or paranasal sinuses of a user with a nasal tip (160).
Figure 8:
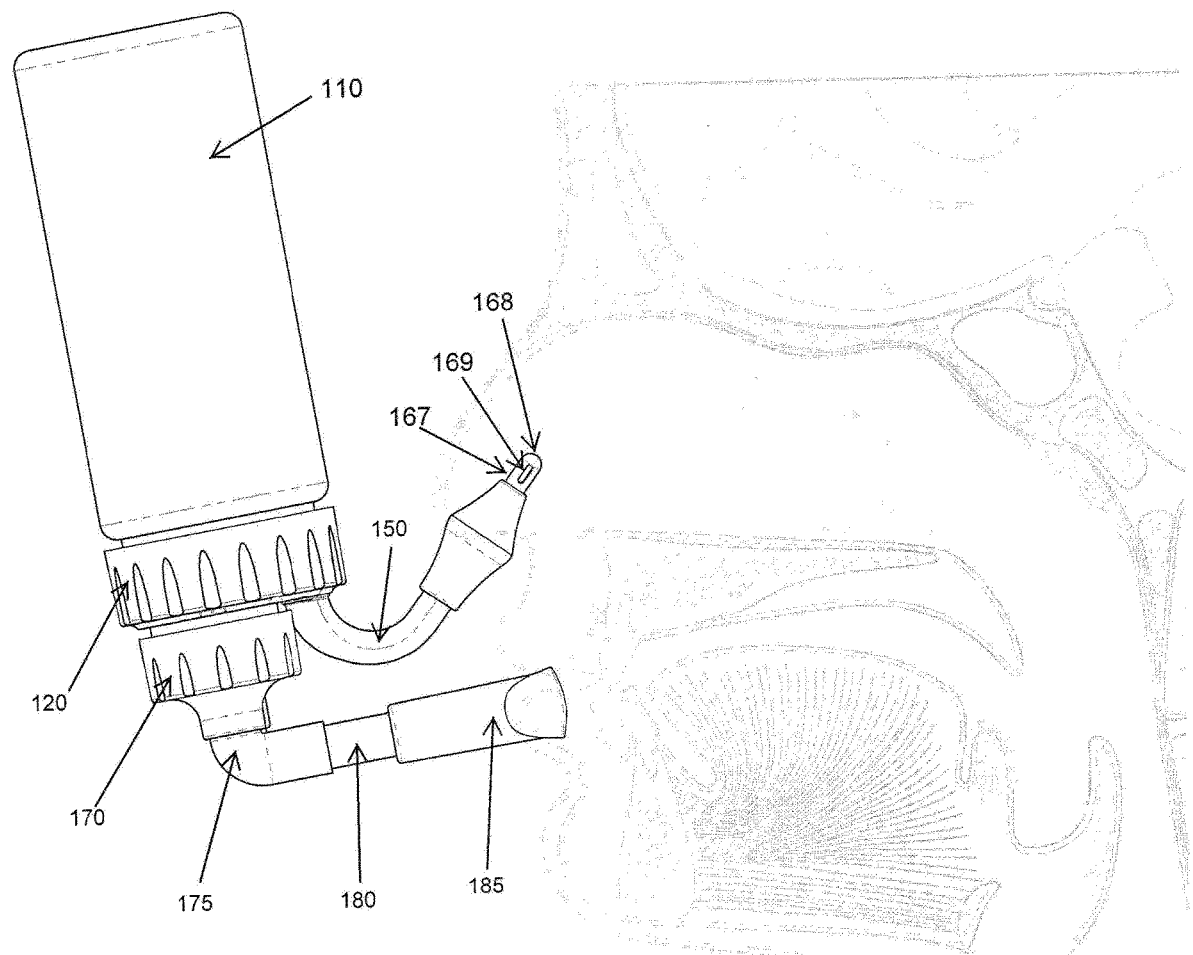
FIG. 8 is a cross-sectional view of a patient's head with an embodiment of the system for delivering an solution to the nasal cavity and or paranasal sinuses of a user with a nasal tip for directional flow (167) adapted to a user's nasal cavity by angling 80° to 90° degrees above the horizontal axis.
Figure 9:
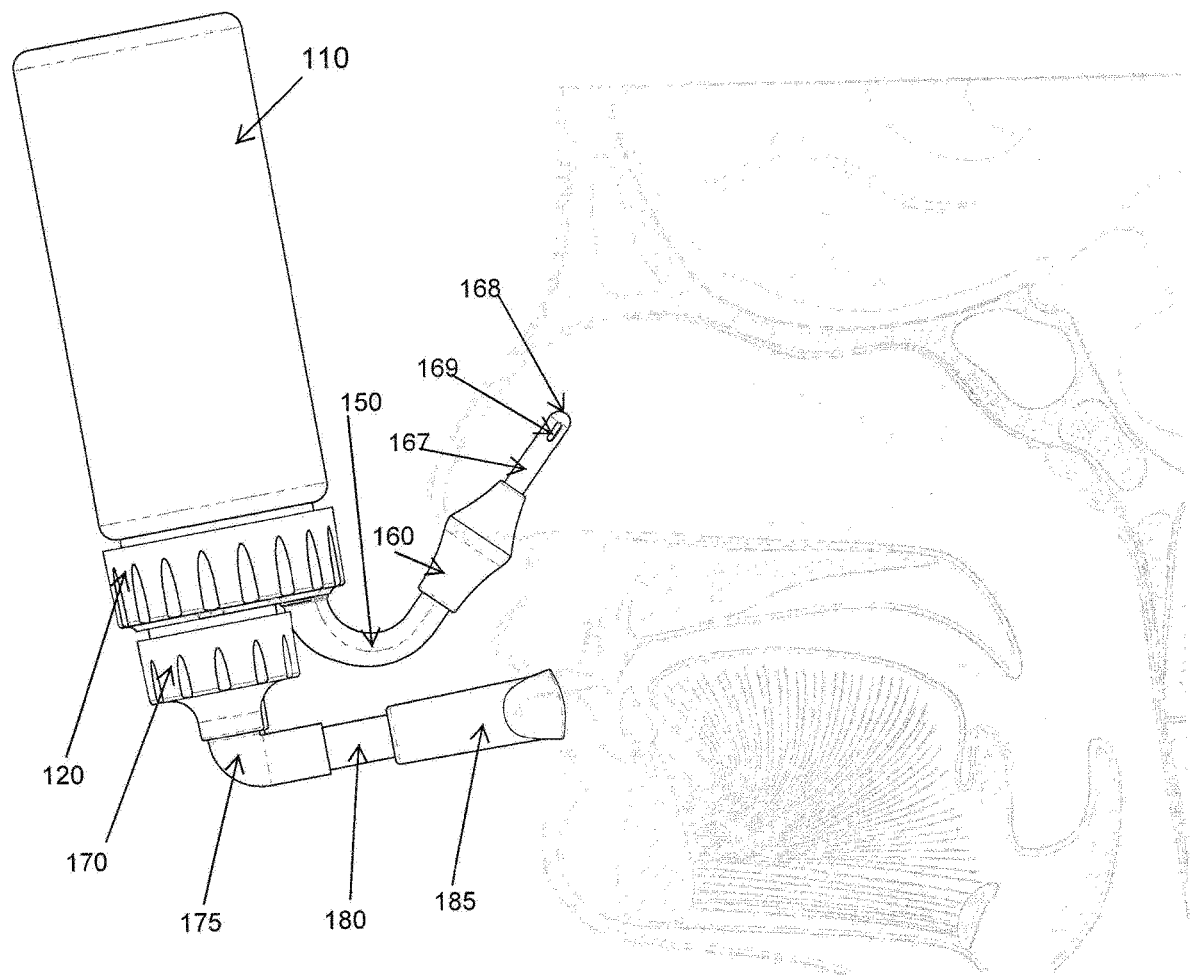
FIG. 9 is a cross-sectional view of a patient's head with an embodiment of the system for delivering an solution to the nasal cavity and or paranasal sinuses of a user with a nasal tip for directional flow (167) adapted to a user's nasal cavity by angling 80° to 90° degrees above the horizontal axis.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting.

While the disclosed subject matter is amenable to various modifications and alternative forms, specific embodiments have been shown by way of example in the drawings and are described in detail below. The intention, however, is not to limit the disclosure to the particular embodiments described. To the contrary, the disclosure is intended to cover all modifications, equivalents, and alternatives falling within the scope of the disclosure as defined by the appended claims.

The term "solution" as used herein means a liquid; water; a pharmaceutically acceptable buffer solution, preferably consisting of a saline solution and more preferably still a sterile saline solution; and, a solution with a therapeutically effective concentration of a pharmaceutical. The pharmaceutical compound portion of the solution may be a salt, solid, liquid, or a gas (including a vapor). The pharmaceutical compound may be selected form any of the biopharmaceutical classes of the Biopharmaceutical Classification System (BCS) where Class 1 has high permeability and high solubility to Class 4 which has low permeability to low solubility. The solution containing a pharmaceutical compound may be an unsaturated solution, a saturated solution, a supersaturated solution, a mixture of two or more substances that are not chemically combined, a homogenous solution, a heterogenous solution, a suspension, or an emulsion.

The use of "including," "comprising," or "having" and variations thereof herein is meant to encompass the items listed thereafter and equivalents thereof as well as additional items.

As the terms are used herein with respect to ranges of measurements (such as those described above), "about" and "approximately" may be used interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various steps disclosed herein unless and except when explicitly referring to the order of individual steps. Additionally, a "set" or "group" of items (e.g. inputs, algorithms, data values, etc.) may include one or more items, and, similarly, a subset or subgroup of items may include one or more items.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

Sino-Nasal Irrigation Device

Referring to FIGS. 1 to 9, the sino-nasal irrigation device (100) consists of a reservoir container (110), a housing (120) that is removably connected to the reservoir container (110) having a grinding chamber (125), a nose tube (150), and an input device (170) that is removably connected to the housing (120).

The reservoir container (110) in the preferred embodiment has a hollow interior cavity adapted to contain an solution and has a base (112). The reservoir container (110) has a curved sidewall (115) that extends substantially perpendicular to the base (112) to the open top (117) of the reservoir container (110) thereby defining the hollow interior cavity. The reservoir container (110) is adapted to removably engage the housing (120). In the preferred embodiment the reservoir container (110) has male threads (118) to threadingly mate with the housing (120). The reservoir container (110) may be of any shape or size including a round bulbous shape, a square or a rectangle.

The housing (120) is removable attachable to the reservoir container (110). In the preferred embodiment the housing (120) has female threads (124) to threadably mate with the reservoir container (110). The top of the housing (122) has a grinding chamber (125) and a nose piece aperture (140). The grinding chamber (125) has a sidewall (128) that is preferably curved and extending substantially perpendicular to the top of the housing (122). The grinding chamber (125) has a filter (135) at the base that is integrated into the housing top (122) consisting of a plurality of holes (138) that will allow ground material of a defined size and water or a solution to pass through the filter (135). The plurality of holes (138) may be of uniform size or varying size. In the preferred embodiment the plurality of holes (138) are of varying size ranging from $\frac{1}{8}^{th}$ of an inch in diameter to $\frac{3}{16}^{th}$ of an inch in diameter.

In an alternative preferred embodiment other substances including powders, liquids, gaseous and vapors may be introduced into the reservoir container (110) through the filter integrated into the grinding chamber (135) or by bypassing the grinding chamber (125) and introduced directly into the solution in the reservoir container (110). In an alternative preferred embodiment a vapor pod (not shown) may be removably attached to the air tube (180) so that when a user exhales into the mouth piece (185) on the input apparatus (170) air and vapor from the vapor pod creates a positive pressure in the air tube (180) and air and vapor passes through the diaphragm (190) and into the reservoir container (110) where the vapor mixes with and dissolves into the solution. The introduction of air and vapor into the reservoir container (110) displacing the solution held in the reservoir container (110) out the nose tube (150) through the nasal tip (160).

The grinding chamber (125) also has a plurality of grinding teeth (130) that extend substantially perpendicular to the filter (135). The plurality of grinding teeth (130) may be of either uniform size and shape or varied size and shape. In the preferred embodiment the plurality of grinding teeth (130) consist of a plurality of cured grinding teeth (131) spaced equal distantly in a circular pattern in the grinding chamber (125) and a plurality of wedge shaped grinding teeth (132) located within the circular pattern formed by the curved grinding teeth (131).

The nose tube (150) is attached to the nose piece aperture (140) in the housing top (122). In the preferred embodiment the nose piece aperture (140) is a curve-linear oval shape. The nose tube (150) is preferably substantially rigid and curved such that when the sino-nasal device (100) is inverted the mouth piece (185) is proximate a user's mouth then the distal end of the nose tube (150) is proximate a user's nose bench. The nose tube (150) has a removable nasal tip (160) at the distal end of the nose tube (150). The nasal tip (160) frictionally engages the nose tube (150) and thus is adjustable and may be positioned in a preferable location for each user. The nasal tip (160) may be removed from the nose tube (150) for cleaning or replacement. The nasal tip (160) has various sizes and shapes (160a-160c) to accommodate the customary nasal opening sizes of children (160a), adults (160b), and larger adults (160c).

An alternative preferred embodiment may include a nasal tip for directional flow (167) that frictionally engage the nose tube (150) or the nasal tip aperture opening (165) to provide for a more controlled and direction application of medicine and/or solution to a surgical site, wound, or by user preference. The nasal tip for directional flow (167) is preferably flexible with a blunt terminal end (168) with a plurality of aperture openings (169) proximate to the terminal end that are preferably 2 to 4 mm in length and more preferably 1 to 2 mm in length. The plurality of aperture openings (169) are preferably oval, but may also be substantially circular or substantially square in order to provide a desired flow rate of solution in a preferred direction. The nasal tip for directional flow (167) are preferably 1 to 4 cm length, and more preferably 1 to 2 cm length. The exposed length of nasal tip for directional flow (167) may also be controlled by how far the nasal tip for directional flow (167) is inserted on the nose tube (150), or alternatively, into the tip aperture opening (165) in order to maximize the delivery of medicine and/or solution to a surgical site, wound, or by preference of a user.

The input apparatus (170) is removably attached to the grinding chamber (125) on the housing (120). In the preferred embodiment the input apparatus (170) has a hollow interior cavity (177) that is threaded to connect to the exterior of the grinding chamber sidewall (128). When the input apparatus (170) is attached to the grinding chamber (125) the mouth piece (185) of the input device (170) should align with the nasal tip (160) of the housing (120) when assembled and closed. The input apparatus (170) is comprised of a mouth piece (185) that is frictionally attached to an air tube (180) so that the location of the mouth piece (185) may be configured in a preferred way for each user. The air tube (180) is also connected to the L-connector (175) of the input apparatus (170). In the preferred embodiment the air tube (180) connects in the center of the top of the L-connector (175) which is attached to the input apparatus (170). A diaphragm (190) is interposed at the terminal end of the air tube (180) where the air tube (180) connects to the input apparatus (170).

When the sino-nasal irrigation device is assembled with a solution in the reservoir container, the diaphragm (190) permits air into the reservoir container (110) when a positive pressure exists in the air tube (180) by allowing air to pass through the diaphragm (190). When a positive pressure does not exist in the air tube (180), then the diaphragm (190) prevents the flow of an solution in the reservoir container (110) from flowing pass the diaphragm (190) and out the input apparatus (170).

The mortar (200) has a first distal end (205) with a recess (210) containing a plurality of grinding teeth (205) and a second distal end (207) with a plurality of tines (prongs) (225) that are covered by a frictionally engaged cap (220). In the preferred embodiment the plurality of grinding teeth (215) in the recess (210) in the first distal end (205) consist of a plurality of curved grinding teeth (215) spaced equal distantly in a circular pattern in the recess (210) and a square pike grinding tooth (210) in the center of the recess (210). The second distal end (207) has a plurality of tines (225) that may be sized or of variable sizes. In the preferred embodiment, the size and placement of the tines (225) matches the aperture size and pattern of the plurality of holes (138) in the filter integrated into the bottom of the grinding chamber (135) to facility the cleaning of the grinding chamber (135) by dislodging any material caught in the integrated filter (135) by pushing the tines (225) into underside of the integrated filter (135) in the housing top (122).

Referring to FIGS. 11 to 14, in an alternative preferred embodiment the reservoir container (610) has a hollow interior cavity adapted to contain an solution and has a threaded base cap (615) to be removably connected to the reservoir container (610). The threaded base cap (615) can withstand direct radiant heating in the range of 75° F. to 150° F. and more preferably 80° F. to 110° F. without any chemical breakdown or leaching of the chemicals used to make the reservoir container (610) or threaded base cap (615). The threaded base cap (615) has a flexible barrier layer (630) that permits a temperature probe (730) from the base station (700) to extend into the reservoir container (610) without coining in direct contact with the solution in the reservoir container (610). The reservoir container (110) has a curved sidewall (115) that extends substantially perpendicular to the base (112) to the open top (117) of the reservoir container (110) thereby defining the hollow interior cavity.

The base station (700) contains a logic engine that permits a user to input the desired temperature a user wants the solution in the reservoir container (610) warmed to. The temperature probe (730) takes a temperature reading, and then compares that temperature reading to the input temperature. If the temperature reading is below the input temperature, then the logic engine provides power to the base station heating sources (720) in order to raise the temperature of the solution to the input temperature. Once the solution reaches the input temperature, the logic engine may reduce power to the base station heating source (720) or turn the base station heating source off. The logic engine will continue to measure the temperature of the solution through the temperature probe (730) and apply heat as needed to maintain temperature. The temperature probe (730) is preferably a thermistor, thermocouple or similar temperature measuring probe. The base station heating source (720) is preferably resistive heating coils but may be any known heating source known to one of ordinary skill in the art.

The alternative preferred embodiment may also have indirect stirring means such as a magnetic stirrer consisting of one or more magnets in the base station and at least one magnet in the reservoir container that may be used to stir the solution to aid the dissolution of difficult to dissolve chemical compounds into solution.

The alternative preferred embodiment may also include an ultra-violate (UV) light source proximately located adjacent to the reservoir container (610) that will sterilize the water in the reservoir container (610).

Method of Using the Sino-Nasal Irrigation Device

The sino-nasal irrigation device (100) may be used by filling the reservoir container (110) with the desired amount of water. Preferably, and recommended, sterile water is used. Alternatively, denatured water may be used. The housing (120) is then removably engaged on the reservoir container (110).

Optionally, if a user wants to use an aqueous saline solution, then the user may place capsule(s) containing the equivalent of 2.4 grains of sodium chloride (NaCl) per 10 ounces of water into the grinding chamber (125) on the housing (120). Then, while firming holding the reservoir container (110), the user engages the first distal end (205) of the mortar (200) with the grinding chamber (125) containing the capsule to grind the capsule and its contents to sufficiently fine size to pass through the filter integrated into the bottom of the grinding chamber (135). Preferably, grinding of a capsule is achieved by twisting the mortar (200) in the grinding chamber (125) while applying downward pressure. Thereby allowing the ground capsule to form an solution in reservoir container (110). If the plurality of holes (138) in the filter (135) have become occluded with remnants of the capsule, then the plurality of holes (138) should be cleared by removing the housing (120) from the reservoir container (110) and pushing the tines (225) on the second distal end of the mortar (207) through plurality of holes from the underside of the integrated filer (135) in the housing top (122) to dislodge any material occluding the filter holes (135). The housing (120) is then removably engaged on the reservoir container (110). In an alternative preferred embodiment other substances including powders, liquids, gaseous and vapors may be introduced into the reservoir container (110) through the filter integrated into the grinding chamber (135) or by bypassing the grinding chamber (125) and directly into the substance into the reservoir container (110), thereby creating an solution.

The input apparatus (170) may then be removably engaged on the housing (120). The mouth piece (185) of the input apparatus (170) is aligned with the nasal tip (160) on the housing (120). The sino-nasal irrigation device (100) is then ready for treatment application.

The sino-nasal irrigation device (100) is then inverted such that the reservoir container (110) is above the input apparatus (170) and the housing (120), the weight of the solution in the reservoir container (110) pushes down on the diaphragm (190) creating a negative pressure on the diaphragm (190). The weight of the solution on the diaphragm (190) prevents air from entering the reservoir container (110) and thus prevents liquid from the reservoir container (110) from flowing out through the nose tube (150). Applying a positive pressure to the bottom of the diaphragm (190) causes the diaphragm to open and allows air to flow into the reservoir container (110). The air flowing into the reservoir container (110) causes turbulence in the solution held in the reservoir container resulting in the mixing of the air and solution. The air flowing into the reservoir container also allows the liquid in the reservoir container (110) to flow out of the reservoir (110) through the nose tube (150) and into a user's nasal cavity. When the positive pressure on the bottom of the diaphragm (190) is removed, the flow of liquid from the reservoir container (110) stops.

When a user, blows or exhales against resistance, the user's soft palate/uvula elevates and contacts the posterior wall of the oro/nasopharynx, thereby closing the choana. This normal physiologic process effectively creates temporary anatomic isolation of the nasal cavity from the oral cavity, distal airway and glottis/proximal trachea. As such, any fluid that is introduced into the user's sino-nasal cavity, as described herein, will remain contained within a user's sino-nasal cavity, being directed out the contralateral sino-nasal cavity, and not travel into the user's distal airway, glottis/superior trachea.

In an alternative preferred embodiment, a user blows or exhales against resistance to close the choana by blowing into the mouth piece (185) on the input apparatus (170), but the tube (180) is partially constrained allowing only a fraction of the air exhaled by the user to reach the reservoir container (110), or is fully constrained such that none of the air exhaled by the user reaches the reservoir container (110). When a positive pressure is detected in the tube (180) due to a user exhaling then a small pump (not shown) is activated to pump solution from the reservoir container (110) out the nose tube (150). When the positive pressure is removed, the pump is deactivated and the flow ceases. This alternative preferred embodiment may be used by those with compromised respiratory systems due to illness or other infirmity.

Figure 10:
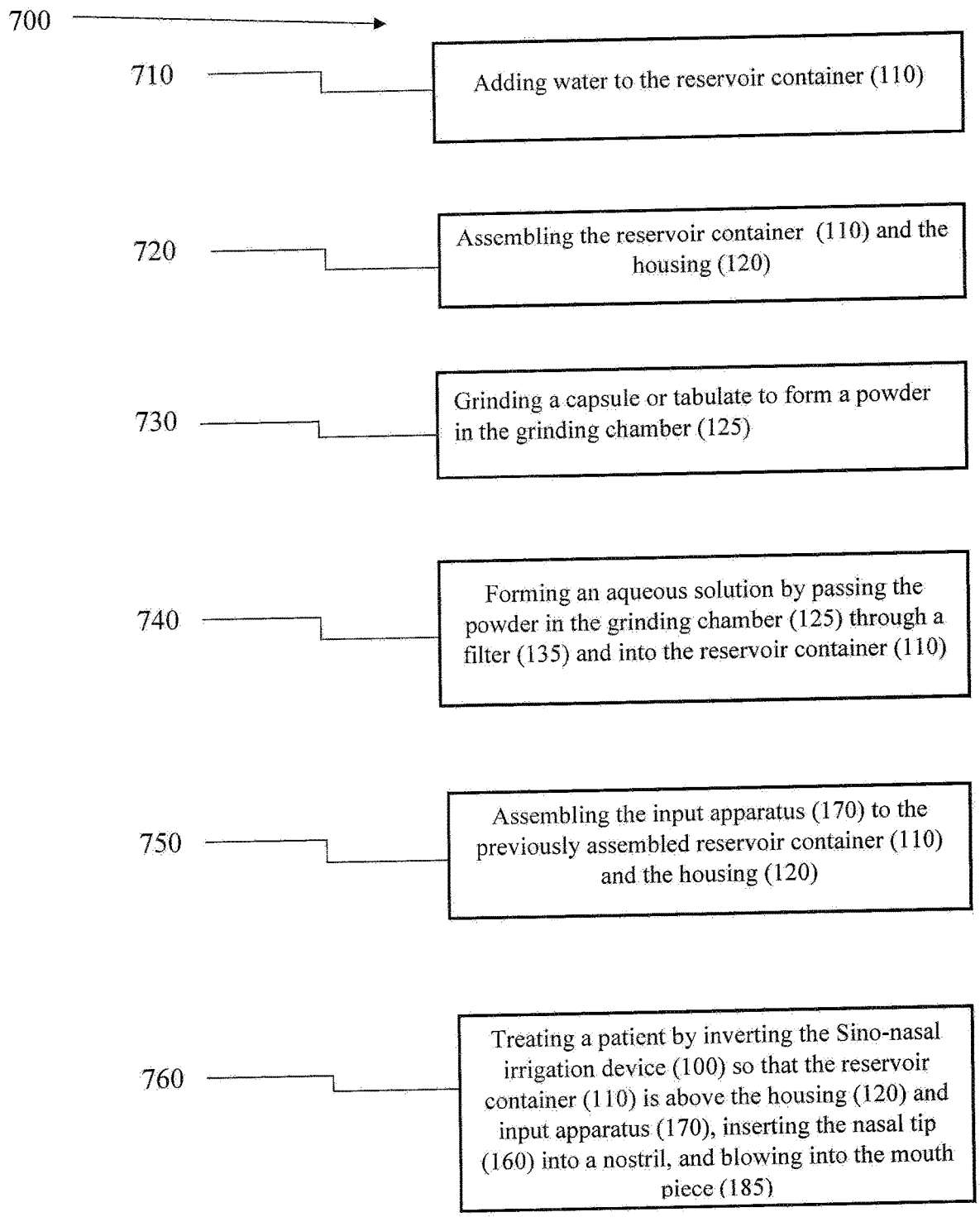
FIG. 10 is a flow chart detailing a preferred method of using the invention disclosed herein.
Figure 11:
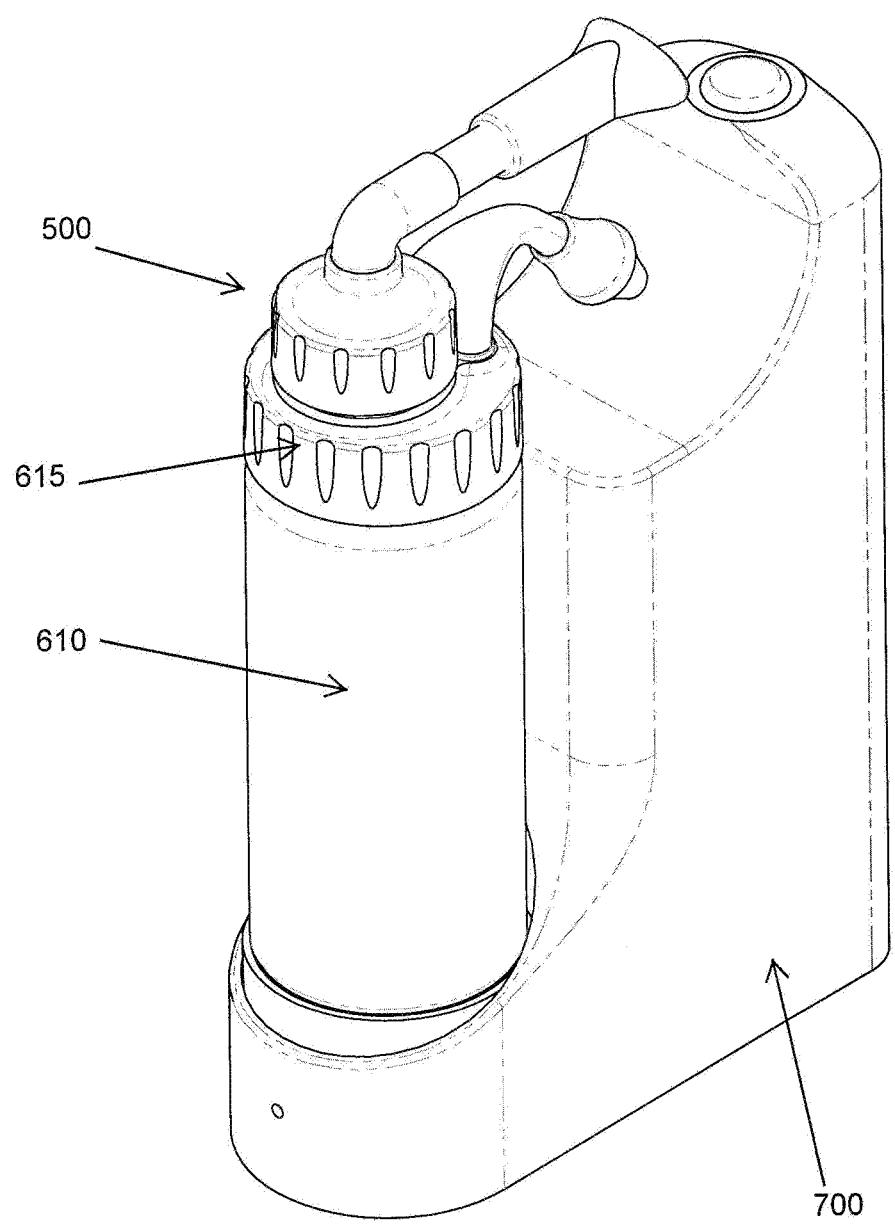
FIG. 11 is a perspective view of an alternative embodiment of illustrative system for delivering an solution to the nasal cavity and or paranasal sinuses of a user with a base for heating and mixing the solution, in accordance with the embodiments of the present disclosure.
Figure 12:
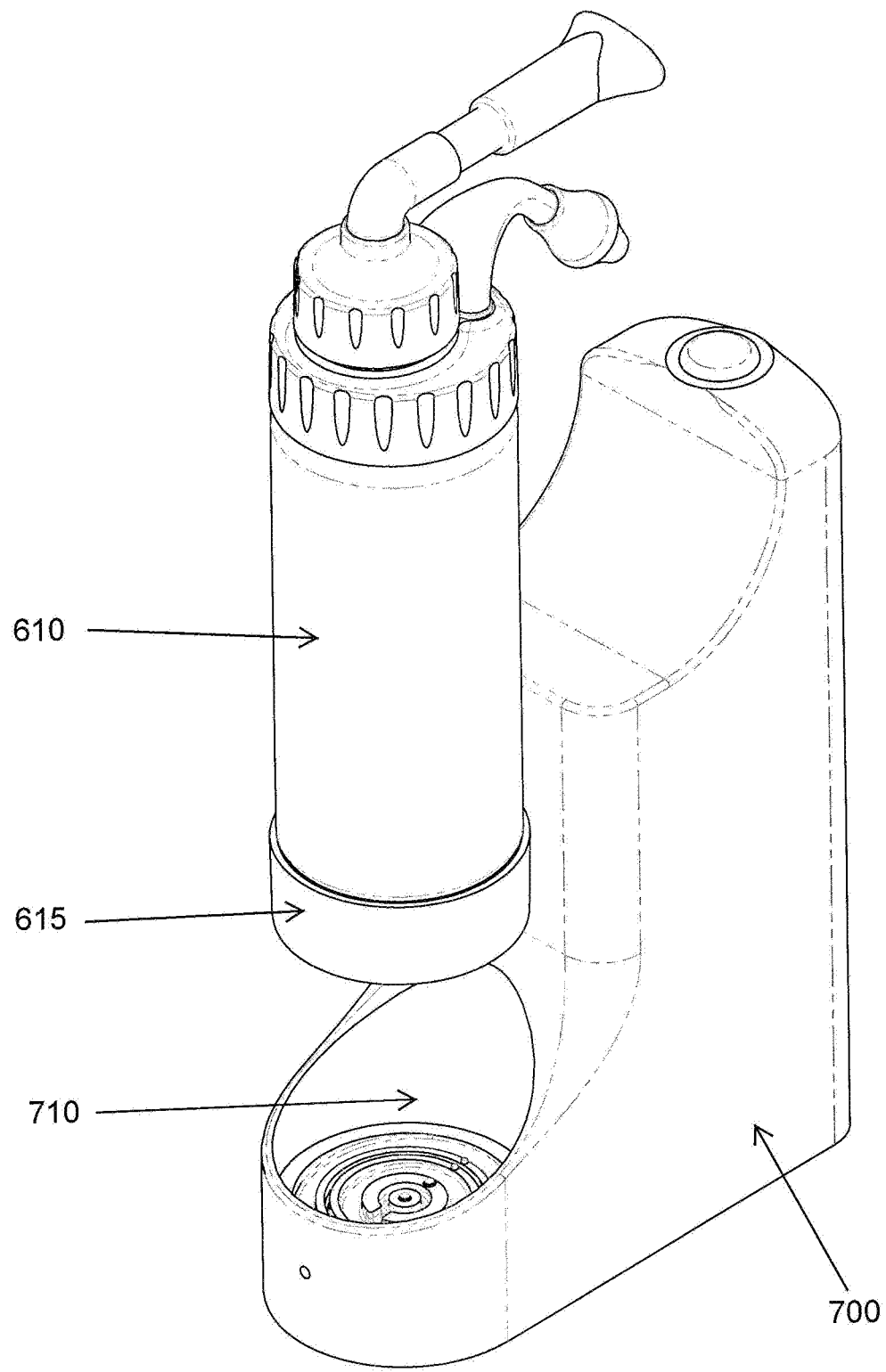
FIG. 12 is a perspective view of an alternative embodiment of illustrative system for delivering an solution to the nasal cavity and or paranasal sinuses of a user with a base for heating and stirring the solution, in accordance with the embodiments of the present disclosure.
Figure 13:
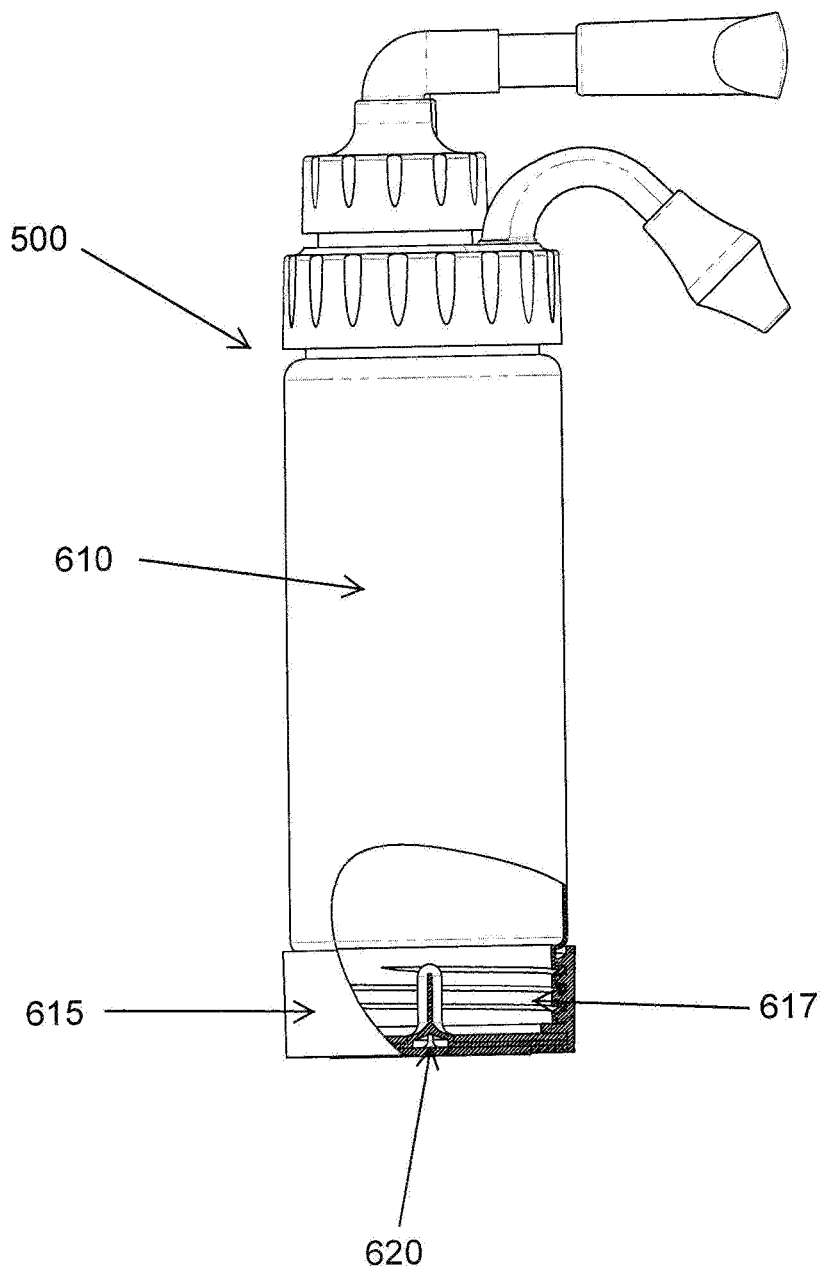
FIG. 13 is a partially exploded perspective view of an alternative embodiment of the illustrative system for delivering an solution to the nasal cavity and or paranasal sinuses of a user with a partial cross-section of the bottom.
Figure 14:
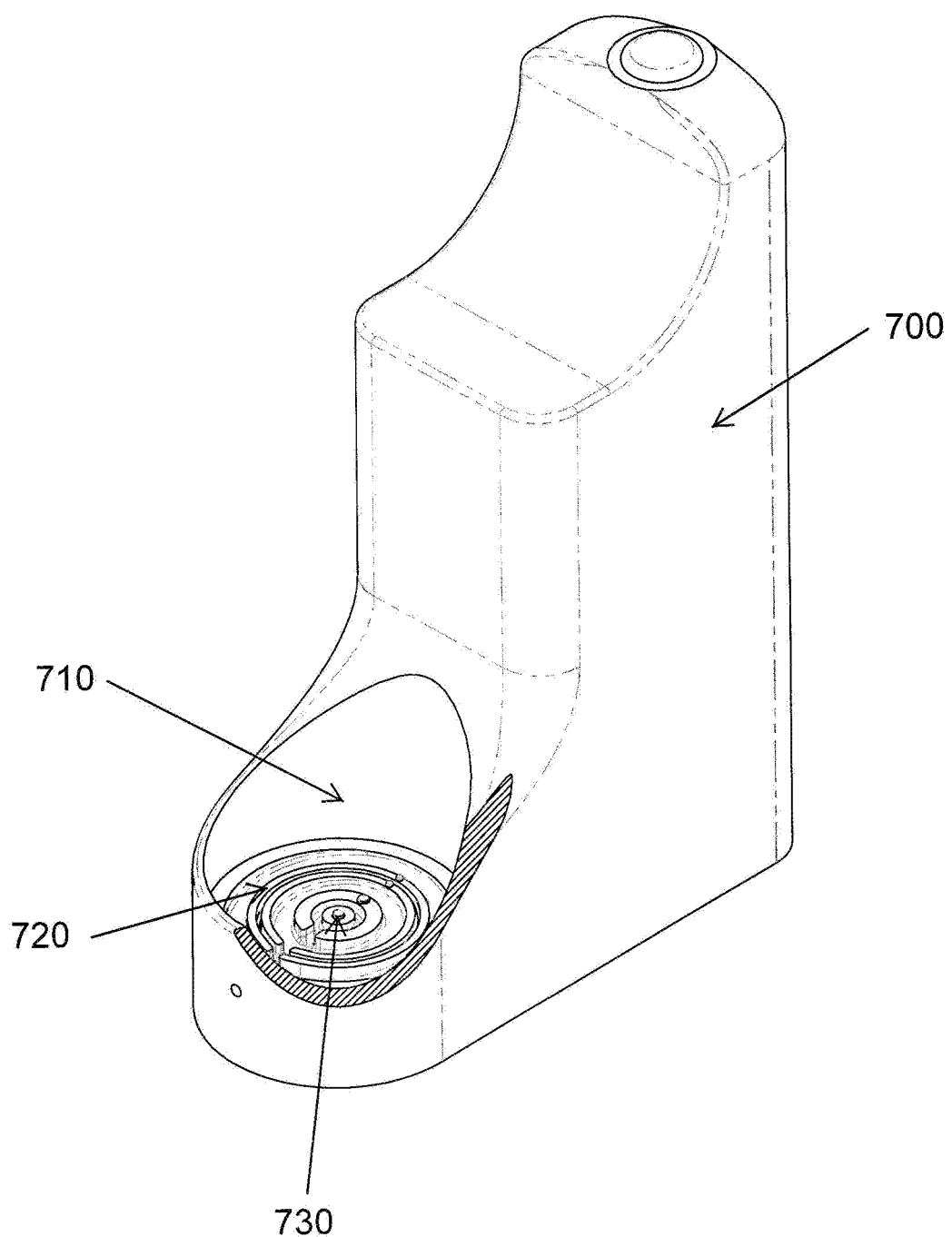
FIG. 14 is a prospective view of the base (700).

Referring to FIG. 10, a method for using the preferred embodiment is provided for treating a patient (700). Block 710 provides for adding a prescribed amount of sterile, or purified, water to the reservoir container (110). Block 720 provides for the partial assembly of the sino-nasal irrigation device by removably connecting the housing (120) to the reservoir container (110). Block 730 grinding of a capsule, tablet, or the like in the grinding chamber (125) to form a powder fine enough to pass through the filter (135). Block 740 provides for the forming of a solution by allowing the ground powder from the capsule, tablet, or the like to pass through the filter (135) and into the reservoir container (110) where the powder will be dissolved into the liquid to form a solution. Block 750 provides for the further assembly of the sino-nasal irrigation device by removably connecting the input apparatus (170) to the previously assembled reservoir container (110) and housing (120). Block 760 provides for the administration of the solution to a user by inverting the assembled sino-nasal irrigation device (100) so that the reservoir container (110) is above the housing (120) and input apparatus (170) such that any air remaining in the reservoir container (110) is proximate the base of the reservoir container (112), inserting the nasal tip (16) into a nostril of the user, and keeping the nasal tip inserted into a nostril of the user, blowing into the mouth piece (185) to provide a positive pressure in the air tube (180). The positive pressure in the air tube (180) causes air to pass through the diaphragm (190) and into the reservoir container (110) thereby displacing the solution held in the reservoir container (110) out the nose tube (150) through the nasal tip (160).

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. For example, the device(s) described in the present) disclosure may be used in conjunction with other medical devices. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, which each claim standing on its own as a separate preferred embodiment of the disclosure.

Moreover, though the general description of the invention has included detailed description of one or more aspects, embodiments, and/or configurations and certain variations and modifications, other variations, combinations, and modifications are within the scope of this disclosure, e.g., as may be within the skill and knowledge of those in the art, after understanding the present disclosure. The intent is to obtain rights which include alternative aspects, embodiments, and/or configurations to the extent permitted, including alternate, inter-changeable and/or equivalent structures, functions, ranges or steps are disclosed herein, and without intending to publicly dedicate any patentable subject matter.

What is claimed is:

1. A device for delivering a solution to a sino-nasal cavity of a user, the device comprising:
    a reservoir container;
    a housing adapted to connect to the reservoir container wherein the housing has a nose tube and a grinding chamber with a filter in the housing and a plurality of grinding teeth extending perpendicular to the filter;
    an input apparatus adapted to connect to the housing wherein the input apparatus has a mouth piece connected to a tube and the tube is connected to a L-connector of the input apparatus; and,
    a mortar with a first end and a second end.

2. The device for delivering the solution to the sino-nasal cavity of the user of claim 1 wherein the mouth piece is removably attached to a first terminal end of the tube and a diaphragm is interposed at the L-connector of the input apparatus.

3. The device for delivering the solution to the sino-nasal cavity of the user of claim 1 wherein the mortar has the first end with a recess containing a plurality of grinding teeth and the second end with a plurality of tines configured to align with a plurality of holes in the filter.

4. The device for delivering the solution to the sino-nasal cavity of the user of claim 3 wherein the mortar further comprises a removable cap that frictionally engages the mortar and covers the tines of the second end of the mortar.

5. The device for delivering the solution to the sino-nasal cavity of the user of claim 1 further comprising a tip with directional flow that is removably attached to a distal end of the nose tube.

6. A device for delivering a solution to a sino-nasal cavity of a user, the device comprising:
    a reservoir container adapted to removably engage a housing wherein the housing has a nose piece with a nasal tip adapted to removably attach to a terminal end of the nose piece;
    an input apparatus with a tube that connects a mouth piece to a L-connector of the input apparatus wherein the mouth piece is adapted to removably connect to the housing; and
    a mortar with a first end with a plurality of grinding teeth and a second end with a plurality of tines.

7. The device for delivering the solution to the sino-nasal cavity of the user of claim 6 wherein the tube has a first terminal end with the mouth piece removably attached and the L-connector of the input apparatus with a diaphragm interposed between the L-connector and a bottom of the input apparatus.

8. The device for delivering the solution to the sino-nasal cavity of the user of claim 7 wherein the diaphragm permits air flow into the reservoir container when a positive pressure exists in the tube.

9. The device for delivering the solution to the sino-nasal cavity of the user of claim 7 wherein the diaphragm prevents gravity flow of the solution from the reservoir container when a positive pressure does not exist in the tube.

10. The device for delivering the solution to the sino-nasal cavity of the user of claim 7 wherein the plurality of tines of the second end of the mortar are configured to match a plurality of holes in a filter.

11. The device for delivering the solution to the sino-nasal cavity of the user of claim 6 further comprising a nasal tip extension with directional flow adapted to removably engage the terminal end of the nose piece or the nasal tip.

12. The device for delivering the solution to the sino-nasal cavity of the user of claim 6 wherein the housing has a grinding chamber with a filter comprising a plurality of holes in the housing.

13. The device for delivering the solution to the sino-nasal cavity of the user of claim 6 wherein the nasal tip is selected from the group consisting of: a nasal tip to accommodate nasal opening sizes of children; a nasal tip to accommodate nasal opening sizes of adults; and, a nasal tip to accommodate nasal opening sizes of larger adults.

14. A device for delivering a solution to a sino-nasal cavity of a user, the device comprising:
    a reservoir container adapted to removably engage a housing wherein the housing has a nose piece with a nasal tip adapted to removably attach to a terminal end of the nose piece;
    the housing further comprising a grinding chamber with a filter in the housing consisting of a plurality of holes in the housing and a plurality of grinding teeth extending perpendicular to the filter; and,
    an input apparatus with a tube with a mouth piece at a first terminal end of the tube and a diaphragm at a second terminal end of the tube that connects to a L-connector of the input apparatus.

15. The device for delivering the solution to the sino-nasal cavity of the user of claim 14 wherein the diaphragm has a first closed position that prevents gravity flow of the solution in the reservoir container when a positive pressure does not exist in the tube and a second open position that permits air flow into the reservoir container when the positive pressure exists in the tube.

16. The device for delivering the solution to the sino-nasal cavity of the user of claim 14 further comprising a nasal tip extension with directional flow adapted to removably engage the terminal end of the nose piece or the nasal tip.

17. The device for delivering the solution to the sino-nasal cavity of the user of claim 14 further comprising a mortar with a first terminal end with a plurality of grinding teeth and a second terminal end with a plurality of tines.

18. The device for delivering the solution to the sino-nasal cavity of the user of claim 17 wherein the plurality of tines of the second terminal end of the mortar are configured to match the plurality of holes of the filter.

* * * * *